US010093598B2

(12) United States Patent
Ou et al.

(10) Patent No.: US 10,093,598 B2
(45) Date of Patent: Oct. 9, 2018

(54) XYLENE SEPARATION PROCESS

(71) Applicants: EXXONMOBIL CHEMICAL PATENTS INC., Baytown, TX (US); GEORGIA TECH RESEARCH CORPORATION, Atlanta, GA (US)

(72) Inventors: John D. Ou, Houston, TX (US); Jeevan S. Abichandani, Houston, TX (US); Yoshiaki Kawajiri, Nagoya (JP); Siwei Guo, Atlanta, GA (US)

(73) Assignees: EXXONMOBIL CHEMICAL PATENTS INC., Baytown, TX (US); GEORGIA TECH RESEARCH CORPORATION, Atlanta, GA (US)

(*) Notice: Subject to any disclaimer, the term of this patent is extended or adjusted under 35 U.S.C. 154(b) by 0 days.

(21) Appl. No.: 15/548,072

(22) PCT Filed: Dec. 28, 2015

(86) PCT No.: PCT/US2015/067701
§ 371 (c)(1),
(2) Date: Aug. 1, 2017

(87) PCT Pub. No.: WO2016/133589
PCT Pub. Date: Aug. 25, 2016

(65) Prior Publication Data
US 2018/0009729 A1    Jan. 11, 2018

Related U.S. Application Data

(60) Provisional application No. 62/118,075, filed on Feb. 19, 2015, provisional application No. 62/242,406, filed on Oct. 16, 2015.

(51) Int. Cl.
C07C 15/08 (2006.01)
C07C 7/13 (2006.01)
(Continued)

(52) U.S. Cl.
CPC .......... *C07C 15/08* (2013.01); *B01D 15/1828* (2013.01); *C07C 7/04* (2013.01); *C07C 7/13* (2013.01); *C07C 15/073* (2013.01)

(58) Field of Classification Search
None
See application file for complete search history.

(56) References Cited

U.S. PATENT DOCUMENTS 3,201,491 A    8/1965   Stine et al.
3,205,166 A    9/1965   Ludlow et al.
(Continued)

OTHER PUBLICATIONS

International Search Report issued in the corresponding application PCT/US2015/067701 dated Mar. 29, 2016.
(Continued)

*Primary Examiner* — Tam M Nguyen
(74) *Attorney, Agent, or Firm* — Roberts Mlotkowski Safran Cole & Calderon, P.C.

(57) ABSTRACT

A process is described for separating paraxylene from a multicomponent fluid mixture of C8 aromatics. A mixture of C8 aromatics is fed to a simulated moving-bed adsorptive apparatus. The location of the feed to the apparatus is moved at set intervals. The rate of flow of feed to the apparatus is varied during each interval to enhance the separation of paraxylene from the multicomponent mixture.

24 Claims, 5 Drawing Sheets

(51) Int. Cl.
*C07C 15/073* (2006.01)
*B01D 15/18* (2006.01)
*C07C 7/04* (2006.01)

(56) References Cited

U.S. PATENT DOCUMENTS

| | | |
|---|---|---|
| 3,761,533 A | 9/1973 | Otani et al. |
| 4,029,717 A | 6/1977 | Healy et al. |
| 4,088,706 A | 5/1978 | Kaeding et al. |
| 4,853,202 A | 8/1989 | Kuznicki |
| 5,001,591 A | 3/1991 | Nakashima |
| 5,102,553 A | 4/1992 | Kearney et al. |
| 5,244,650 A | 9/1993 | Kuznicki et al. |
| 5,365,004 A | 11/1994 | Beck et al. |
| 6,369,287 B1 | 4/2002 | Magne-Drisch et al. |
| 8,283,274 B2 | 10/2012 | Cheng et al. |
| 8,529,757 B2 | 9/2013 | Go et al. |
| 2005/0167365 A1 | 8/2005 | Schramm et al. |
| 2012/0264994 A1* | 10/2012 | Hurst ............... C07C 7/13 585/831 |
| 2013/0153501 A1 | 6/2013 | Frey et al. |
| 2014/0171715 A1* | 6/2014 | Corradi ............ B01D 3/141 585/800 |

OTHER PUBLICATIONS

Kawajiri et al., "Optimization strategies for simulated moving bed and PowerFeed processes", AIChE J. vol. 52 (2006) B, pp. 1343-1350.

Zhang et al., "PowerFeed operation of simulated moving bed units: changing flow-rates during the switching interval", Journal of Chromatography A. 1006, pp. 87-99, 2003, Elsevier B.V.

M. Minceva, and A. E. Rodrigues, 'Modeling and Simulation of a Simulated Moving Bed for the Separation of P-Xylene', Industrial & Engineering Chemistry Research, 41 (2002), 3454-61.

Silva et al. Chemical Engineering & Technology, 37 (2014) 1541-1551.

* cited by examiner

XYLENE SEPARATION PROCESS

CROSS-REFERENCE TO RELATED APPLICATIONS

The present application is a U.S. National Phase of PCT/US2015/067701 filed on Dec. 28, 2015 claiming priority to provisional U.S. Patent application No. 62/118,075 filed Feb. 19, 2015 and provisional U.S. Patent application No. 62/242,406 filed Oct. 16, 2015. The disclosure of the PCT Application is hereby incorporated by reference into the present Application.

FIELD OF THE INVENTION

The invention relates to a process for separating at least one C8 aromatic from a mixture of at least two C8 aromatics by means of a simulated moving-bed adsorption apparatus.

BACKGROUND OF THE INVENTION

Of the three xylene isomers, paraxylene is the most commercially valuable. However, due to the similarity of their boiling points, adsorption is a commonly used method to separate paraxylene from the other xylene isomers, in which an adsorbent solid which preferentially adsorbs paraxylene over metaxylene and orthoxylene is used.

A commercial embodiment of a simulated moving-bed adsorption apparatus is used in the well-known Parex™ Process, which is used to separate C8 aromatic isomers and provide a more highly pure paraxylene (PX) from a less highly pure mixture. See by way of example U.S. Pat. Nos. 3,201,491; 3,761,533; and 4,029,717. Other embodiments involving a simulated moving-bed adsorption apparatus include ELUXYL™, available from Axens, and AROMAX™, available from Toray.

In a Parex™ unit, the locations of liquid input and output are moved by a fluid directing device described herein as a rotary valve device. This device may comprise one or more rotary valves, as well as various control and accessory means, such as inlet lines, outlets lines and valves associated therewith. The rotary valve device works in conjunction with conduits located between the adsorbent beds. The rotary valve device accomplishes moving the input and output locations through first directing the liquid introduction or withdrawal lines to specific conduits in fluid communication with particular adsorbent beds. After a specified time period, called the step time, the rotary valve device advances one index and redirects the liquid inputs and outputs to the conduit immediately adjacent and downstream of the previously used conduits. Each advancement of the rotary valve device to a new position is generally called a valve step, and the completion of all the valve steps is called a valve cycle. The step time or step interval is uniform for each valve step in a valve cycle, and may be from about 30 seconds to 4 minutes.

An example of a commercial simulated moving-bed adsorption apparatus contains 24 adsorbent beds and 24 conduits individually connected to a bed and providing fluid communication with the rotary valve device. The conduits of the adsorption apparatus may function, over time, as at least two liquid input lines (e.g., a feed input line and a desorbent input line) and two liquid output lines (e.g., an extract withdrawal line and a reformate withdrawal line).

A system employing a simulated countercurrent flow process such as described in U.S. Pat. Nos. 3,201,491; 3,761,533; 4,029,717; and 8,529,757 are shown in FIG. 1, along with several modifications. The diagram in FIG. 1 will be understood by those of skill in the art to depict a simulated moving-bed process. Desorbent is introduced through conduit 100. Liquid withdrawal stream leaves the apparatus through conduit 101. Extract (containing the desired product) leaves the apparatus via conduit 102. Raffinate leaves the apparatus through conduit 110. A C8 aromatic feed, which comprises 15 to 30 volume percent paraxylene, is added to the apparatus through conduit 107. Optionally, a C8 aromatic mixture, which comprises 75 to 98 volume percent paraxylene, is added as an additional feed through conduit 108.

Not shown in the drawing, but as would be recognized by one of skill in the art in possession of the disclosure of U.S. Pat. No. 8,529,757, is one or more distillation towers and attendant pumps and conduits, which may be utilized to purify the liquid withdrawal stream leaving the above-described apparatus via conduit 101.

Continuing with the description of FIG. 1, the arrow 112 represents the simulated movement of beds upward through apparatus 120 containing plural adsorption bed chambers $A_1$ through $A_{n+j}$. Arrow 111 represents the countercurrent flow of circulating bulk fluid to the adsorbent beds. In operation, the adsorbent does not flow, but the various inlet and outlet streams, such as feed, product and flush streams, cycle through the adsorbent bed chambers, represented by chambers $A_1$ through $A_{n+j}$, in a direction, which is countercurrent to the simulated movement of adsorbent beds and cocurrent to the direction of the circulating bulk fluid. This simulates the movement of the adsorbent beds $A_1$ through $A_{n+j}$. Theoretically, there may be any number of adsorbent beds, thus n>2 and n+j is the maximum number of adsorbent beds. However, from a practical standpoint the number of bed lines is limited by design considerations and other factors. It will be understood that n and j are positive integers and that in an example of a commercial embodiment the total number of adsorbent beds is 24, and thus n+j typically may be 24. Certain adsorbent beds, i.e., beds between $A_2$ and $A_n$, beds $A_{n+3}$, $A_{n+5}$, $A_{n+6}$, and $A_{n+10}$ through $A_{n+j-1}$ are not depicted in FIG. 1, for convenience of view.

In the unit shown in FIG. 1, xylene and ethylbenzene molecules from feed 107 are adsorbed in bed $A_{n+9}$. As the adsorbent in bed $A_{n+9}$ becomes saturated with C8 aromatics, a portion of the C8 aromatics in the feed flow along with circulating bulk fluid and flow into at least one bed, such as $A_{n+10}$ (not shown in FIG. 1), below bed $A_{n+9}$. According to a predetermined cycle time, the flow of feed, along with the flows of other inlet and outlet streams, is shifted to one adsorbent bed below. In FIG. 1 the bed below $A_{n+9}$ would be bed $A_{n+10}$ (not shown in FIG. 1). The direction of the shifting of feed and other streams to and from the adsorbent apparatus is the same as the direction of the flow of the circulating bulk fluid through the apparatus. This shifting of streams results in adsorbed C8 aromatics being moved (in a simulated manner) to beds above the bed to which feed is being introduced at any given time.

The feed which is introduced through conduit 107 may comprise equilibrium xylenes (such as from a powerformer, isomerization unit or transalkylation unit). Such equilibrium xylenes may comprise about 21-24 wt % paraxylene (PX). A portion of the feed introduced through conduit 107, may also comprise enhanced paraxylene, for example, from a selective toluene disproportionation unit (0 unit). This enhanced paraxylene may comprise, for example, about 85-90 wt % PX. In one embodiment, the feed to introduce through conduit 107 is free of enhanced paraxylene from a toluene disproportionation process.

The paraxylene is desorbed from adsorbent in the beds by desorbent, which is introduced into bed $A_1$ of the adsorption apparatus through conduit 100. The desorbent displaces paraxylene from the adsorbent. The desorbent also has a different boiling point than the C8 aromatics and is easily separated from C8 aromatics in a distillation process. Examples of desorbents include paradiethylbenzene (pDEB), toluene (TOL), or a mixture thereof. The stream, which is introduced into the apparatus through conduit 100, may, optionally, also comprise a diluent, such as a non-aromatic (NA) hydrocarbon, which has less binding affinity to the adsorbent than any of the C8 aromatics. However, such diluents take up volume in the apparatus and are not necessary. Accordingly the stream, which is introduced into the apparatus through conduit 100, is preferably free of such diluent.

An extract stream is withdrawn from bed $A_n$ through conduit 102. The extract stream comprises a mixture of the purified paraxylene and the desorbent. As shown in FIG. 1, the withdrawal point of the extract stream though conduit 102 is between the point of introduction of the feed through conduit 107 and the point of introduction of the desorbent through conduit 100. A raffinate stream is withdrawn from bed $A_{n+j}$ through conduit 110. The raffinate stream comprises paraxylene-depleted C8 aromatics and desorbent.

FIG. 1 depicts a simplified simulated moving-bed apparatus, wherein countercurrent "movement" of the solids in beds $A_1$ through $A_{n+j}$ relative to the fluid streams may be simulated by the use of a rotary valve, which is not shown in the FIG. 1. As the valve rotates, the zones previously discussed move through the column in a stepwise sequence due to the change in the stream flows through the valve. In certain embodiments, a rotary valve, as described in U.S. Pat. No. 3,205,166, may be used. In this arrangement, each fluid communication conduit connected to the chamber may serve a different function with each step rotation of the rotary valve.

In standard simulated moving-bed separation processes, the flow rate of streams into and out of the simulated moving-bed are held constant during the step time. However, modulation of flow during the step time has been found to enhance separation in certain instances involving simulated moving-bed separation of fructose and glucose or separation of 1,1'-bi-2-naphthol enatiomers. The enhanced separation may result in greater purity of product streams or less desorbent use. This process for modulating flow rates during a step time has been referred to as a PowerFeed process. Examples of PowerFeed processes are described in an article by Kawajiri et al., "Optimization strategies for simulated moving bed and PowerFeed processes", AIChE J. Vol. 52 (2006) B, pp. 1343-1350, and in an article by Zhang et al., "PowerFeed operation of simulated moving bed units: changing flow-rates during the switching interval", Journal of Chromatography A. 1006, pp. 87-99, 2003, Elsevier B.V.

There is an ongoing need to further improve the simulated moving-bed adsorption process, maximize the purity of product streams and make the process more efficient.

SUMMARY OF THE INVENTION

The present invention is directed to using a PowerFeed process to enhance the separation of at least one C8 aromatic from a mixture of at least two C8 aromatics in a simulated moving-bed (SMB) unit. This enhanced separation may cause one or more desirable results, such as increased product purity, decreased desorbent loading in the unit, decreased desorbent feed to the unit, decreased desorbent to feed ratio, increased feed rate, increased unit capacity, increased throughput and/or increased recovery given a constant SMB configuration and size. The use of PowerFeed may also reduce the number of beds needed in the unit to maintain industry performance standards. Reducing the number of SMB unit beds lowers capital costs.

In the claimed process, at least one C8 aromatic is separated from a mixture of at least two C8 aromatics by simulated moving-bed adsorptive separation. It will be understood that a C8 aromatic is an aromatic compound having 8 carbon atoms, such as paraxylene, metaxylene, orthoxyxlene and ethylbenzene. The process comprises steps (a) to (f).

In step (a), a feed stream, which comprises at least two C8 aromatics, is introduced into a simulated moving-bed adsorptive apparatus comprising multiple beds containing adsorbent material. In step (b), a desorbent stream, which comprises desorbent, is also introduced into the simulated moving-bed adsorptive apparatus. In step (c), an extract stream, which comprises desorbent and at least one C8 aromatic, is withdrawn from the simulated moving-bed adsorptive apparatus. In step (d), at least one raffinate stream, which comprises at least one C8 aromatic, which is different from the C8 aromatic in the extract stream of step (c), is withdrawn from the simulated moving-bed adsorptive apparatus. In step (e), a flow of circulating fluid is maintained throughout the simulated moving-bed adsorptive apparatus. Steps (a) to (e) take place simultaneously.

In step (f), the flow of streams into and out of the simulated moving-bed adsorptive apparatus is switched to a bed downstream in terms of the direction of the circulating fluid. This switching occurs at a set time interval, which is referred to herein as time interval X. During time interval X the rate flow of feed introduced in step (a) is varied, as opposed to being held constant.

The process may be used to separate paraxylene from a C8 aromatic mixture of paraxylene, orthoxylene, metaxylene and ethylbenzene. For example, the mixture of at least two C8 aromatics may comprise paraxylene, orthoxylene, metaxylene and ethylbenzene, and the extract stream of step (c) may comprise paraxylene.

The process may also be used to separate ethylbenzene from a C8 aromatic mixture of orthoxylene, metaxylene and ethylbenzene. For example, the mixture of at least two C8 aromatics may comprise orthoxylene, metaxylene and ethylbenzene, and the extract stream of step (c) may comprise ethylbenzene.

The rate of flow of streams into and out of a simulated moving-bed adsorption apparatus may be varied one or more times during time interval X. At the beginning of time interval X, the flow rates into and out of the simulated moving-bed adsorption apparatus may be held constant for a portion or subinterval of interval X. After the expiration of a first portion of X, the flow rate of the at least one of the streams is changed. Time interval X may be split into at least two portions or subintervals. The durations of each of the subintervals may be the same or different. Properly varying the flow rate of the feed leads to enhanced separation and an improved process, as compared to maintaining a constant feed flow rate during time interval X.

DETAILED DESCRIPTION

Figure 1:
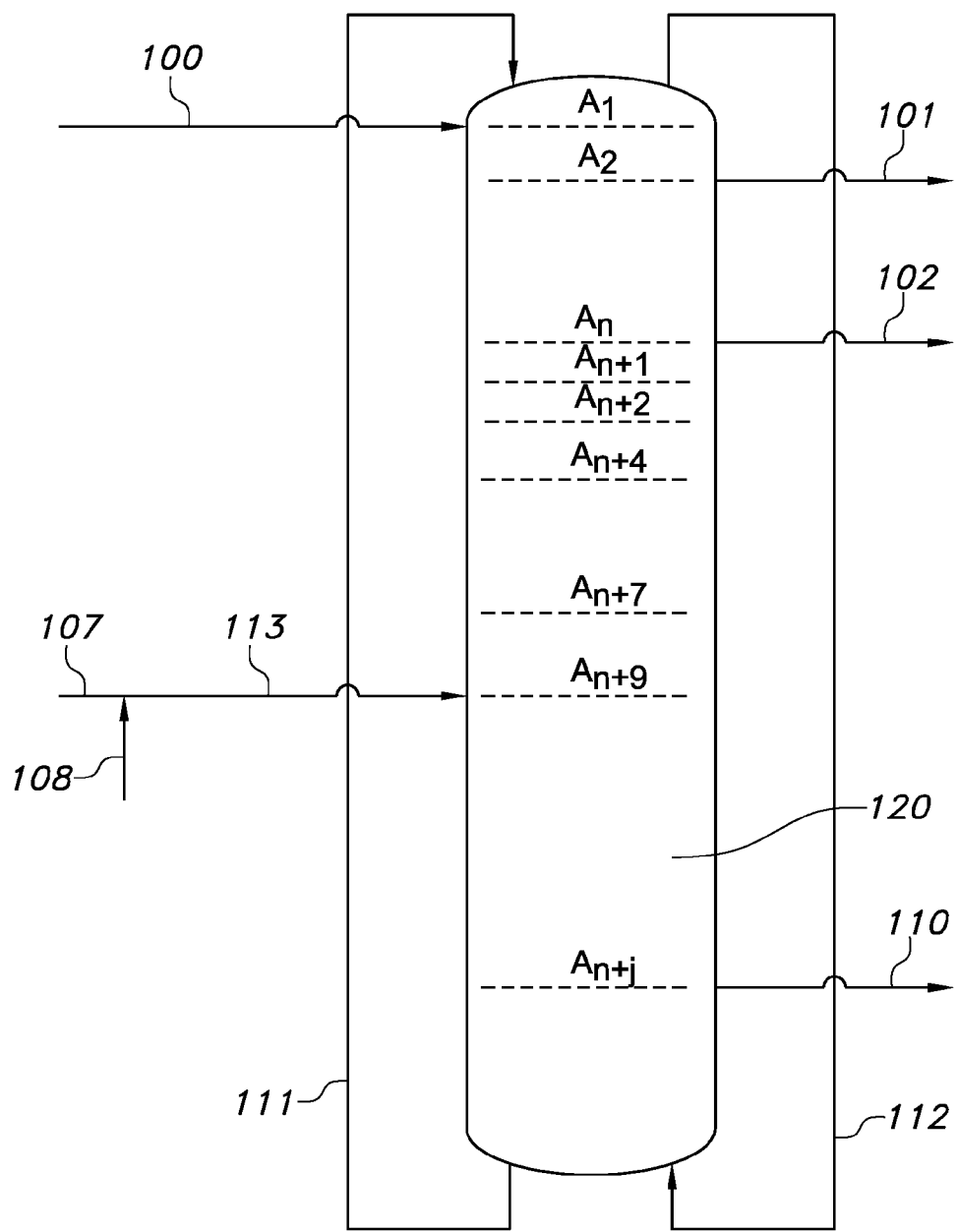
FIG. 1 is a schematic illustration of a simulated moving-bed adsorptive separation system.

The present invention involves using a PowerFeed process to enhance the separation of at least one C8 aromatic from a mixture of at least two C8 aromatics.

Definitions

Various terms used in this description will be understood in the context of this description. A further explanation of certain terms used herein is provided below.

C8 aromatics are aromatic compounds having 8 carbon atoms. Examples of C8 aromatics include paraxylene, metaxylene, orthoxylene and ethylbenzene.

Equilibrium xylene is a mixture of C8 aromatics having a thermodynamic equilibrium concentration of the various C8 aromatic compounds when the C8 aromatics are subjected to non-selective isomerization conditions. Equilibrium xylene may be produced in a non-selective process for producing xylenes. A non-selective process for producing xylenes may involve reacting reactants over a non-selective catalyst. Equilibrium xylene may be produced, for example, in a xylene isomerization process, a transalkylation process or a reforming process. Equilibrium xylene may also be produced by other processes. Equilibrium xylene may comprise, for example, about 23 percent paraxylene, based on the total of the xylenes.

Enhanced paraxylene is a mixture of C8 aromatics having a greater concentration of paraxylene than equilibrium xylene Enhanced paraxylene may be produced in a selective process for producing xylenes. A selective process for producing xylenes may involve reacting reactants over a selective catalyst. Enhanced paraxylene may be produced, for example, by a selective toluene disproportion process or a selective toluene alkylation process. Enhanced paraxylene may also be produced by other processes Enhanced paraxylene may have a concentration of, for example, at least 75% paraxylene, based on the total of C8 aromatics.

A non-selective process for producing xylenes is a process which produces equilibrium xylenes. A non-selective process for producing xylenes may take place over a non-selective catalyst. Examples of non-selective catalysts include large pore zeolites, such as zeolite X and zeolite Y, or amorphous aluminosilicates. When toluene is disproportionated over a large pore size zeolite, equilibrium zeolites may be produced.

A selective process for producing paraxylene (PX) is a process which produces paraxylene in preference to other xylene isomers (MX and OX). A selective process for producing paraxylene may be produced, for example, by a catalytic process over a paraxylene selective catalyst. Examples of paraxylene selective catalysts include medium pore size zeolites, such as ZSM-5, modified with selectivating agents. Selectivating agents may neutralize surface catalytic sites or narrow the pores of the catalyst. Examples of paraxylene selective catalysts and selectivating agents are provided by in U.S. Pat. No. 5,365,004, International Publication No. WO 2013/330093, and U.S. Pat. No. 4,088,706.

Circulating bulk fluid is the fluid (i.e. liquid) which flows in a continuous manner through a simulated moving-bed adsorption apparatus. The concentration of compounds in this circulating bulk fluid changes as this fluid flows through the apparatus due to, inter alia, adsorption and desorption of xylenes, ethylbenzene and desorbent, withdrawal of fluids in extract and reformate streams, and introduction of fluids through feed, desorbent and flush streams.

A liquid distribution device is a device which distributes the flow of stream into and out of a simulated moving-bed adsorptive device. A liquid distribution device may comprise a rotary valve or a system of other types of valves, such as the system used in the ELUXYL™ process.

A rotary valve device is a device comprising at least one rotary valve. The rotary valve device may comprise various control and accessory means, such as inlet lines, outlet lines and valves associated therewith.

A simulated moving-bed adsorption apparatus is an apparatus including beds of adsorbent stacked in at least one column. In operative use of the adsorption apparatus, the beds are connected in a fluid and circular manner in series with one another.

A simulated countercurrent absorptive separation is a separation which takes place in a simulated moving-bed adsorption apparatus.

An adsorbent column is an apparatus having adsorbent beds stacked one on top of the other.

An adsorbent bed chamber is a chamber in an adsorption apparatus containing a bed of adsorbent (i.e., adsorbent bed).

An adsorbent bed is a bed of adsorbent contained within an adsorbent bed chamber. An adsorbent column includes multiple adsorbent beds. An adsorbent apparatus has one or more adsorbent columns. Any fluid in an adsorbent bed chamber, whether or not adsorbed on an adsorbent, is considered to be part of the bed. Accordingly, when fluid is introduced into or withdrawn from an adsorbent bed chamber, the fluid is considered as being introduced or withdrawn, into or from the bed itself.

An adsorbent is a solid material, which selectively adsorbs at least one C8 aromatic in preference to C8 aromatics. In a simulated moving-bed apparatus, such as a Parex™ unit, examples of adsorbents include charcoal, ion-exchange resins, silica gel, activated carbon, zeolitic material, and the like. An adsorbent, which is particularly useful for separating paraxylene from other C8 aromatics, is a faujasite-type molecular sieve material, such as zeolite X or zeolite Y, optionally, substituted or treated with an enhancing agent, such as a Group I or II element, such as potassium or barium. Examples of adsorbents for separating paraxylene from other C8 aromatics are described in U.S. Pat. No. 3,761,533. An example of an adsorbent for separating ethylbenzene from metaxylene and orthoxylene is a titanosilicate adsorbent, as described in U.S. Pat. Nos. 6,369,287; 5,244,650; 5,001,591; and 4,853,202.

A desorbent is a liquid, which displaces C8 aromatics from adsorbent. The desorbent may be equally or slightly more preferentially adsorbed on the adsorbent than paraxylene. The desorbent may have a greater sorbate affinity for the adsorbent than other C8 aromatics. The desorbent should have a boiling point significantly different than the boiling points of C8 aromatics, such that the desorbent may be separated from C8 aromatics by distillation. Examples of desorbents for a paraxylene separation process include paradiethylbenzene and toluene.

Unless otherwise specified herein, the terms, downstream and upstream, refer to the direction of flow of circulating bulk fluid.

A number of abbreviations are used herein. PX stands for paraxylene. MX stands for metaxylene. OX stands for orthoxylene. EB stands for ethylbenzene. pDEB stands for paradiethylbenzene. TOL stands for toluene. NA stands for non-aromatics. Non-aromatics, such as paraffins, may be introduced into an adsorption apparatus as a feed impurity, especially when the feed comprises C8 aromatics obtained from a reforming process.

Inventive Process

The simulated moving-bed adsorptive separation may take place in an apparatus comprising multiple beds containing adsorbent material, i.e., multiple adsorbent bed chambers, stacked one on top of the other. A circulating bulk fluid may flow in a continuous manner into the top of an adsorbent bed chamber, through the adsorbent bed and down to the top of the next adsorbent bed chamber. Separate conduits may provide fluid communication between each adsorbent bed chamber and a liquid distribution device, such as at least one rotary valve.

The flow of liquids through conduits to and from adsorbent bed chambers may be controlled by the liquid distribution device, such that, over time, each of steps (a), (b), (c), and (d) take place in each of the adsorbent bed chambers of the apparatus. The apparatus comprising multiple adsorbent bed chambers may comprise from 5 to 50, for example, from 5 to 32, for example, from 5-20, for example 8 adsorbent bed chambers.

At the same time that the C8 aromatic feed is passed through a liquid distribution device through a first conduit into an adsorbent bed in a first adsorbent bed chamber according to step (a), steps (b), (c) and (d) occur in other chambers and conduits of the adsorption apparatus.

The multicomponent feed of step (a) may comprise a C8 aromatic mixture of paraxylene, orthoxylene, metaxylene and ethylbenzene. This C8 aromatic mixture of step (a) may comprise equilibrium xylenes with a concentration of paraxylene from 15 to 30 volume percent, for example, from 15 to 27 volume percent, for example, from 21 to 24 volume percent. The multicomponent feed of step (a) may also comprise enhanced paraxylene having a concentration of from 70 to 85 volume percent, for example, from 70 to 80 volume percent, paraxylene.

When ethylbenzene is separated from metaxylene and/or orthoxylene, the feed may comprise at least 5 weight percent ethylbenzene, less than 2 weight percent paraxylene, and at least 50 weight percent of the sum of metaxylene and orthoxylene.

According to one embodiment, at least 50 volume percent of the C8 aromatic mixture may be produced by at least one refinery or petrochemical process. Examples of refinery or petrochemical processes for producing equilibrium xylenes for the multicomponent feed of step (a), which mixture comprises from 15 to 30 volume percent of paraxylene, include a reforming process, an isomerization process, a transalkylation process and a mixture of any of these processes. An example of a refinery or petrochemical process for producing enhanced paraxylene, which comprises from 75 to 98 volume percent of paraxylene, which may be used as the multicomponent feed of step (a) or as part of a flushing medium, is a selective toluene disproportionation process, a selective benzene or toluene methylation process, or a selective process for converting methanol to paraxylene.

The desorbent, introduced into the simulated moving-bed adsorption apparatus via the desorbent stream, may comprise, for example, paradiethylbenzene, toluene or tetralin. A tetralin desorbent is described in U.S. Pat. No. 8,283,274.

When paraxylene is separated from a mixture of C8 aromatics, the extract stream withdrawn according to step (c) may comprise at least 99.7 volume percent of paraxylene, based on the total volume of xylenes and ethylbenzene present in the extract stream. The extract stream may be separated by distillation downstream to provide a purified paraxylene product and a stream rich in desorbent, which may be recycled to for re-use in the simulated moving-bed adsorptive process.

One or more raffinate streams may be withdrawn from the simulated moving-bed adsorptive apparatus. When a single raffinate stream is withdrawn from a simulated moving-bed adsorption apparatus for separating paraxylene, the raffinate stream may comprise desorbent, metaxylene, orthoxylene and ethylbenzene. This raffinate stream is withdrawn from a bed of the simulated moving-bed adsorptive separation unit through a conduit and then through a liquid distribution device, such as a rotary valve. The bed, from which the raffinate stream is withdrawn, is downstream, based on the direction of the flow of circulating bulk fluid, from the bed into which feed is introduced.

The raffinate stream may be distilled to obtain a stream enriched in desorbent and a stream enriched in C8 aromatics, such as metaxylene, orthoxylene and ethylbenzene. The desorbent may be recycled for re-use in the simulated moving-bed adsorptive process. The C8 aromatics from the distillation may be isomerized in the liquid phase, vapor phase, or a combination thereof. In particular, these C8 aromatics may be passed to an isomerization unit to obtain an isomerized product stream comprising from 15 to 30 volume percent, for example, from 20 to 30 volume percent of paraxylene. The isomerized product stream may then be recycled to the simulated moving-bed adsorptive apparatus.

When at least two raffinate streams are withdrawn from the simulated moving-bed adsorptive apparatus for separating paraxylene, a first raffinate stream may comprise ethylbenzene and desorbent, and a second raffinate stream may comprise orthoxylene, metaxylene and desorbent. The first raffinate stream may be distilled to obtain a stream enriched in desorbent and a stream enriched in ethylbenzene, which may be subjected to ethylbenzene isomerization conducted in the vapor phase, ethylbenzene dealkylation conducted in the vapor phase, or purged to fuel gas. The second raffinate stream may be distilled to obtain a stream enriched in desorbent and a stream enriched in metaxylene and orthoxylene, which may be isomerized, preferably in the liquid phase, and recycled to the simulated moving-bed adsorptive apparatus. The desorbent may be recycled for re-use in the simulated moving-bed adsorptive process.

In an embodiment in which the at least one C8 aromatic feed further comprises n-nonane, three raffinate streams may be withdrawn from the simulated moving-bed adsorptive apparatus. The first raffinate stream may comprise ethylbenzene and desorbent. The second raffinate stream may comprise orthoxylene, metaxylene and desorbent. The third raffinate stream may comprise n-nonane and desorbent. The first and second raffinates may be treated as disclosed above and the third raffinate may be distilled to recover the desorbent for re-use.

The rate of flow of streams into and out of simulated moving-bed adsorption apparatus may be varied at least once during time interval X. At the beginning of time interval X, the flow rates into and out of the simulated moving-bed adsorption apparatus may be held constant for a portion or subinterval of interval X. After the expiration of a first portion of X, the flow rates of at least one of the streams may be changed. Time interval X may be split into at least two portions or subintervals. The durations of each of the subintervals may be the same or different. For example, according to one embodiment described in Examples herein, time interval X is split up into four different portions of unequal duration.

Especially when a single raffinate stream is withdrawn from a simulated moving-bed adsorptive apparatus, more of the at least one C8 aromatic feed may be introduced into the simulated moving-bed adsorptive apparatus during the latter portion of time interval X than in the earlier portion of time interval X. For example, if X is 60 seconds, the flow of feed to a bed of the simulated moving-bed adsorptive apparatus is switched every 60 seconds. When more of the at least one multicomponent feed is introduced into the simulated moving-bed adsorptive apparatus during the latter portion of time interval X than in the earlier portion of time interval X, and X is 60 seconds, less of the total feed introduced during the 60 seconds would be introduced during the first 30 seconds of X, and more of the total feed introduced during the 60 seconds would be introduced during the last 30 seconds of X.

In a particular embodiment, less than 30% of the at least one multicomponent feed may be introduced into the simulated moving-bed adsorptive apparatus during a time subinterval of from 0 to 40% of X, and at least 70% of the at least one multicomponent feed may be introduced into the simulated moving-bed adsorptive apparatus during a time subinterval of from 40 to 100% of X. According to this embodiment, if X is 60 seconds, less than 30% of the at least one multicomponent feed would be introduced into the simulated moving-bed adsorptive apparatus during the first 20 seconds of X, and at least 70% of the at least one multicomponent feed may be introduced into the simulated moving-bed adsorptive apparatus during the last 40 seconds of X.

In another embodiment, the flow of feed may be described in terms of five (5) subintervals of X. In particular, (1) less than 10% of the feed, which is introduced in time interval X, may be introduced during a time subinterval of from 0 to 20% of X, (2) less than 15% of the feed, which is introduced in time interval X, may be introduced during a time subinterval of from 20 to 40% of X, (3) at least 15% of the feed, which is introduced in time interval X, may be introduced during a time subinterval of from 40 to 60% of X, (4) at least 20% of the feed, which is introduced in time interval X, may be introduced during a time subinterval of from 60 to 80% of X, and (5) at least 20% of the feed, which is introduced in time interval X, may be introduced during a time subinterval of from 80 to 100% of X. According to this embodiment, if X is 60 seconds, (1) less than 10% of the feed, which is introduced in time interval X, would be introduced during the first 12 seconds of X; (2) less than 15% of the feed, which is introduced in time interval X, would be introduced during a time subinterval of from 12 to 24 seconds from the start of X; (3) at least 15% of the feed, which is introduced in time interval X, would be introduced during a time subinterval of from 24 to 36 seconds from the start of X, (4) at least 20% of the feed, which is introduced in time interval X, would be introduced during a time subinterval of from 36 to 48 seconds from the start of X, and (5) at least 20% of the feed, which is introduced in time interval X, would be introduced during a time subinterval of from 48 to 60 seconds from the start of X. After 60 seconds the flow of feed to a bed would be interrupted and resumed in the next bed downstream in terms of the flow of circulating fluid in the simulated moving-bed adsorptive apparatus.

The flow rate of other streams may also be varied during time interval X. For example, less of the raffinate stream may be withdrawn from the simulated moving-bed adsorptive apparatus during the latter portion of time interval X than in the earlier portion of time interval X. For example, if X is 60 seconds, the flow of raffinate from a bed of the simulated moving-bed adsorptive apparatus is switched every 60 seconds. When less of the raffinate is withdrawn from the simulated moving-bed adsorptive apparatus during the latter portion of time interval X than in the earlier portion of time interval X, and X is 60 seconds, less of the total raffinate withdrawn during the 60 seconds would be withdrawn during the last 30 seconds of X, and more of the total raffinate would be withdrawn during the 60 seconds would be withdrawn during the first 30 seconds of X.

In a particular embodiment, at least 60% of the raffinate may be withdrawn from the simulated moving-bed adsorptive apparatus during a time subinterval of from 0 to 40% of X, and less than 40% of the raffinate may be withdrawn from the simulated moving-bed adsorptive apparatus during a time subinterval of from 40 to 100% of X. According to this embodiment, if X is 60 seconds, at least 60% of the raffinate would be withdrawn from the simulated moving-bed adsorptive apparatus during the first 20 seconds of X, and less than 40% of the raffinate may be withdrawn from the simulated moving-bed adsorptive apparatus during the last 40 seconds of X.

In another embodiment, the flow of raffinate may be described in terms of five (5) subintervals of X. In particular, (1) at least 25% of the raffinate, which is withdrawn in time interval X, may be withdrawn during a time subinterval of from 0 to 20% of X; (2) at least 25% of the raffinate, which is withdrawn in time interval X, may be withdrawn during a time subinterval of from 20 to 40% of X; (3) less than 15% of the raffinate, which is withdrawn in time interval X, may be withdrawn during a time subinterval of from 40 to 60% of X; (4) less than 15% of the raffinate, which is withdrawn in time interval X, may be withdrawn during a time subinterval of from 60 to 80% of X; and (5) less than 20% of the raffinate, which is withdrawn in time interval X, may be withdrawn during a time subinterval of from 80 to 100% of X. According to this embodiment, if X is 60 seconds, (1) at least 25% of the raffinate, which is withdrawn in time interval X, would be withdrawn during the first 12 seconds of X; (2) at least 25% of the raffinate, which is withdrawn in time interval X, would be withdrawn during a time subinterval of from 12 to 24 seconds from the start of X; (3) less than 15% of the raffinate, which is withdrawn in time interval X, would be withdrawn during a time subinterval of from 24 to 36 seconds from the start of X; (4) less than 15% of the raffinate, which is withdrawn in time interval X, would be withdrawn during a time subinterval of from 36 to 48 seconds from the start of X, and (5) less than 15% of the raffinate, which is withdrawn in time interval X, would be withdrawn during a time subinterval of from 48 to 60 seconds from the start of X. After 60 seconds the flow of raffinate from a bed would be interrupted and resumed in the next bed downstream in terms of the flow of circulating fluid in the simulated moving-bed adsorptive apparatus.

The flow rate of the extract stream may also be varied during time interval X. For example, less than 30% of the extract may be withdrawn from the simulated moving-bed adsorptive apparatus during a time subinterval of from 0 to 40% of X, and at least 70% of the extract may be withdrawn from the simulated moving-bed adsorptive apparatus during a time subinterval of from 40 to 100% of X. According to this embodiment, if X is 60 seconds, less than 30% of the extract would be withdrawn from the simulated moving-bed adsorptive apparatus during the first 20 seconds of X, and at least 70% of the raffinate may be withdrawn from the simulated moving-bed adsorptive apparatus during the last 40 seconds of X.

In another embodiment, the flow of extract may be described in terms of five (5) subintervals of X. In particular, (1) less than 15% of the extract, which is withdrawn in time interval X, may be withdrawn during a time subinterval of from 0 to 20% of X; (2) less than 15% of the extract, which is withdrawn in time interval X, may be withdrawn during a time subinterval of from 20 to 40% of X; (3) at least 15% of the extract, which is withdrawn in time interval X, may be withdrawn during a time subinterval of from 40 to 60% of X; (4) at least 20% of the extract, which is withdrawn in time interval X, may be withdrawn during a time subinterval of from 60 to 80% of X; and (5) at least 20% of the extract, which is withdrawn in time interval X, may be withdrawn during a time subinterval of from 80 to 100% of X. According to this embodiment, if X is 60 seconds, (1) less than 15% of the extract, which is withdrawn in time interval X, would be withdrawn during the first 12 seconds of X; (2) less than 15% of the extract, which is withdrawn in time interval X, would be withdrawn during a time subinterval of from 12 to 24 seconds from the start of X; (3) at least 15% of the extract, which is withdrawn in time interval X, would be withdrawn during a time subinterval of from 24 to 36 seconds from the start of X; (4) at least 20% of the extract, which is withdrawn in time interval X, would be withdrawn during a time subinterval of from 36 to 48 seconds from the start of X, and (5) at least 20% of the extract, which is withdrawn in time interval X, would be withdrawn during a time subinterval of from 48 to 60 seconds from the start of X. After 60 seconds the flow of extract from a bed would be interrupted and resumed in the next bed downstream in terms of the flow of circulating fluid in the simulated moving-bed adsorptive apparatus.

Operating the simulated moving bed apparatus with PowerFeed allows for the reduction of adsorbent beds needed to obtain an efficient separation. In one embodiment, the number of beds containing adsorbent material in the simulated moving-bed adsorptive apparatus is 16 or less. The ratio of the volume, in terms of $m^3$ of adsorbent in each bed, to the number of beds in the simulated moving-bed adsorptive apparatus is at least 1. Each bed may have a cross-sectional area of from 10 to 15 $m^2$. The number of beds containing adsorbent material in the simulated moving-bed adsorptive apparatus may be, for example, 16, 12 or 8.

When the number of beds containing adsorbent material in the simulated moving-bed adsorptive apparatus is 16, the ratio of the volume, in terms of $m^3$ of adsorbent in each bed to the number of beds in the simulated moving-bed adsorptive apparatus, may be from 1.2 to 1.6. When the number of beds containing adsorbent material in the simulated moving-bed adsorptive apparatus is 12, the ratio of the volume, in terms of $m^3$ of adsorbent in each bed to the number of beds in the simulated moving-bed adsorptive apparatus, may be, for example, from 2.3 to 2.7. When the number of beds containing adsorbent material in the simulated moving-bed adsorptive apparatus is 8, the ratio of the volume, in terms of $m^3$ of adsorbent in each bed to the number of beds in the simulated moving-bed adsorptive apparatus, may be, for example, from 5.5 to 5.9.

According to an inventive embodiment provided herein, there is also provided a simulated moving bed apparatus. This apparatus comprises: (i) from 8 to 16 bed chambers for containing adsorbent material; (ii) a fluid distribution device for introducing a feed stream into one of the beds, introducing a desorbent stream into one of the beds, withdrawing an extract stream from one of the beds, and withdrawing a raffinate stream from one of the beds, wherein the fluid distribution device comprises a first control mechanism for switching the flow of streams to other beds after a set time interval; and (iii) a second control mechanism for adjusting the rate of flow of streams into and out of beds during the set time interval.

EXAMPLES

In Examples which follow, a computer model is used to simulate separation of paraxylene from other C8 aromatics in a Parex™ unit. The unit comprises two columns in fluid communication with a rotary valve device. Each column comprises twelve adsorbent bed chambers, stacked one on top of the other, containing a molecular sieve adsorbent. For the purposes of explanation, these beds are identified as beds 1 to 24. The number of beds described in each zone is for illustrative purposes and the number of beds may be varied without changing the concepts described herein.

In the first column, the beds are stacked, such that fluid, which is introduced into the top of a first column, flows downward through the top of the column to the bed (i.e., bed 1) at the top of the stack of beds and then through beds below to the bed (i.e., bed 12) at the bottom of the column Fluid from the bottom end of the first column then flows to the top of a second column. Fluid, which is introduced into the top of the second column, flows downward through the column to the bed (i.e., bed 13) at the top of the stack of beds to the bed (i.e., bed 24) at the bottom of the column. Fluid from the bottom end of the second column then flows to the top of a first column to complete a circulation loop of circulating bulk fluid throughout the columns.

When feed is first introduced into the adsorption apparatus, this initial introduction of feed may take place in any of the beds of the apparatus. For example, feed may be introduced to the top of the first column. The feed is primarily composed of C8 aromatics having 23 percent paraxylene and 77 percent of a mixture of metaxylene, orthoxylene and ethylbenzene. The feed also includes small amounts of impurities including toluene and paraffins. The feed may be a mixture of product streams from a reforming process, a transalkylation process and an isomerization process.

Feed, which is introduced into the top of the first column, becomes adsorbed in the adsorbent in the first catalyst bed. The adsorbent in the adsorption apparatus is a molecular sieve adsorbent. Feed may continue to be introduced into the first adsorbent bed until at least a portion of the feed is carried downward with the flow of circulating bulk fluid to the second catalyst bed (i.e., bed 2) and even as far as the third adsorbent bed (i.e., bed 3).

As feed stream is being fed into bed 1, a liquid withdrawal stream is taken from the end of bed 6, a desorbent stream is introduced into the top of bed 10, and another withdrawal stream is taken from the end of bed 15. The desorbent introduced into the adsorption apparatus is paradiethylbenzene.

After a predetermined period of time, a rotary valve device shifts the flow of these streams. In each shift, the flow of these streams is redirected to a bed immediately downstream, in terms of the direction of circulating fluid through the columns. In particular, in a first shift, the flow of feed stream is redirected from bed 1 to bed 2, the flow of liquid withdrawal stream from bed 6 is redirected to bed 7, the flow of desorbent into bed 10 is redirected to bed 11, and the flow of liquid withdrawn from bed 15 is redirected to bed 16. Each shift of the direction of stream flow is also referred to as a valve step.

In the initial stages of feed introduction, e.g., during the start-up stage of the unit, there is an insufficient amount of C8 aromatics to advance downstream to the point where liquid is first withdrawn from the circulating bulk fluid. Also, in these initial stages, there have been an insufficient number of valve steps to push beds with C8 aromatics upstream to the point between the introduction of the desorbent and the introduction of feed, where a second withdrawal stream is taken. However, as the rotary valve device controlling these streams advances through a sufficient number of valve steps, the number of beds comprising C8 aromatics downstream and upstream from the bed to which feed is introduced increases.

Eventually, liquid C8 aromatics will be present in each of the beds downstream of the bed to which feed is introduced and the bed where a first withdrawal stream is taken. The circulating bulk fluid will become increasingly depleted in paraxylene in beds located furthest downstream from the bed to which feed is introduced. Eventually, the liquid withdrawn from the bed located 6 beds downstream from the bed to which feed is introduced, will have a concentration of paraxylene, based on the total of C8 aromatics, of less than about 1-2 percent, typically paraxylene recoveries are greater than 95%. At this point in time, the stream withdrawn from the bed, which is six beds downstream from the bed to which feed is introduced, may be characterized as a raffinate stream.

After sufficient number of valve steps of the process has taken place, liquid C8 aromatics will be present in each of the beds upstream of the bed to which feed is introduced and the bed where a second withdrawal stream is taken. The circulating bulk fluid will become increasingly enriched in paraxylene in beds located furthest upstream from the bed to which feed is introduced. Eventually, the liquid withdrawn from the bed located 10 beds upstream from the bed to which feed is introduced, will have a concentration of paraxylene, based on the total of C8 aromatics, of greater than about 99 percent. At this point in time, the stream withdrawn from the bed, which is ten beds upstream from the bed to which feed is introduced, may be characterized as an extract stream.

When a sufficient number of valve steps of the process have taken place to establish raffinate and extract streams, the beds of the apparatus may be described in terms of four zones, i.e., a desorption zone, a purification or rectification zone, an adsorption zone and a buffer zone. The desorption zone may include the bed to which a desorbent stream is introduced and four beds downstream from this bed terminating in the bed from which the extract stream is withdrawn. The purification zone may include nine beds immediately downstream of desorption zone, terminating with the bed immediately upstream from the bed to which feed is introduced. The adsorption zone may include the bed to which feed is introduced and six beds immediately downstream of the purification zone terminating in the bed from which a raffinate stream is withdrawn. The buffer zone may include six beds immediately downstream from the purification zone and terminating in the bed immediately upstream from the desorption zone. The number of beds in each zone may vary from the numbers described above.

The raffinate and extract streams may pass through conduits and through a rotary valve device. These streams may then be distilled to separate desorbent from C8 aromatics. A paraxylene product may be recovered from the distillation of the extract stream. Desorbent recovered by distillation of the extract stream may be recycled to the adsorption process. C8 aromatics obtained by distillation of the raffinate stream may be passed to an isomerization unit to convert a portion of these C8 aromatics to paraxylene. The isomerized C8 aromatics may then be used as a portion of the feed to the adsorption process. Desorbent recovered by distillation of the raffinate stream may also be recycled to the adsorption process.

The computer model takes into account the possibility of providing the adsorption zone with one or more flush streams. For example, a first or primary flush stream may pass through the rotary valve device and through a conduit to displace residual feed in the conduit into a bed, which is two beds upstream, in terms of the direction of flow of circulating fluid, from the bed to which feed is introduced. For example, when feed is introduced to bed 1, the primary flushing fluid could be introduced into bed 23. The primary flush stream may be shifted one bed downstream, in terms of the direction of the flow of the circulating fluid, along with other inlet and withdraw streams with each valve step of the process.

A second or secondary flush stream may also pass through the rotary valve device and through a conduit to displace residual primary flush fluid in the conduit into a bed, which is nine beds upstream, in terms of the direction of flow of circulating fluid, from the bed to which feed is introduced. The bed to which the secondary flush stream may be directed is also one bed downstream, in terms of the direction of the flow of circulating bulk fluid, from the bed from which an extract stream is withdrawn. For example, when feed is introduced to bed 1, the primary flush fluid would be directed to bed 23, the secondary flush fluid would be directed to bed 16, and the extract stream would be taken from bed 15.

A liquid withdrawal stream may also be taken from the desorption zone. In particular, the liquid withdrawal stream may be taken from the bed located one bed downstream from the bed to which the desorbent stream is introduced. For example, when feed is introduced to bed 1, the primary flush fluid would be directed to bed 23, the secondary flush fluid would be directed to bed 16, the extract stream would be taken from bed 15, the liquid withdrawal stream would be taken from bed 11, and the desorbent stream (i.e., a paradiethylbenzene stream) would be introduced to bed 10.

In Examples 1-4, which follow, separation takes place in a simulated moving-bed apparatus having 24 beds. Paradiethylbenzene is used as the desorbent. The desorption zone has six beds, the adsorption zone has nine beds, the purification zone has six beds, and the buffer zone has three beds. The length of each bed is 113.5 cm, the diameter of each bed is 411.7 cm, and the volume of each bed is $15.1 \times 10^6$ cm$^3$.

Example 1 (Comparative)

In this Example, the mass transfer coefficient, k, is 0.5 min$^{-1}$. The flow rates of the inlet and outlet streams are held constant over each step interval. Each step interval (i.e., the duration during which streams are introduced and withdrawn from the simulated moving-bed ad sportive apparatus between switching intervals) is 2.92 minutes.

During each step, 10.4 m$^3$ of desorbent and 4.4 m$^3$ of feed are introduced into the simulated moving-bed adsorptive apparatus, and 8.9 m$^3$ of extract and 5.9 m$^3$ of raffinate are withdrawn from the simulated moving-bed adsorptive apparatus.

In this Example, a separation of 1.49 m³/min of feed (0.00295 m³/min/kg-adsorbent) is achieved with a desorbent to feed ratio (D/F) of 2.39.

Example 2

Figure 2:
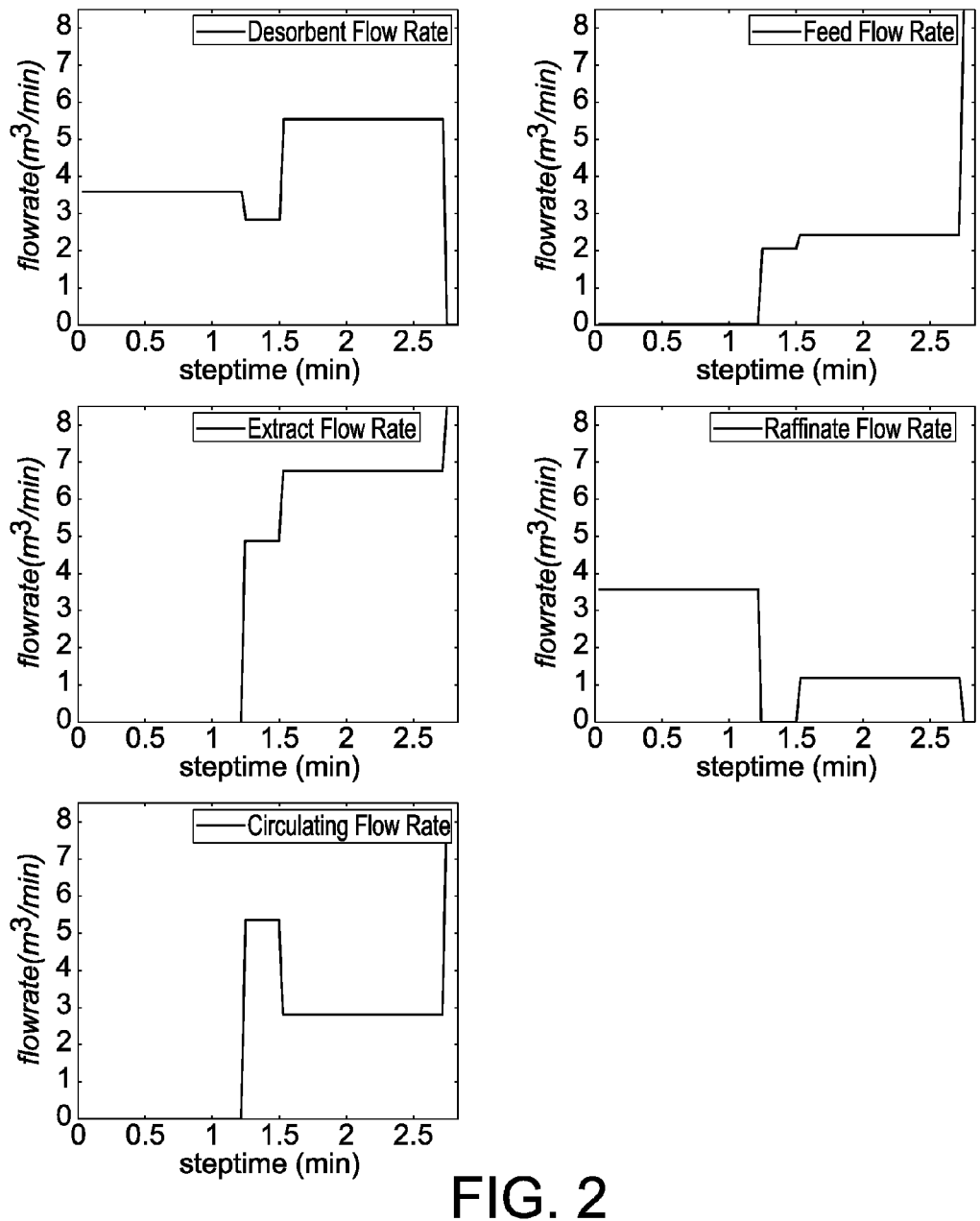
FIG. 2 shows plots of flow rates of streams during a step interval.
Figure 3:
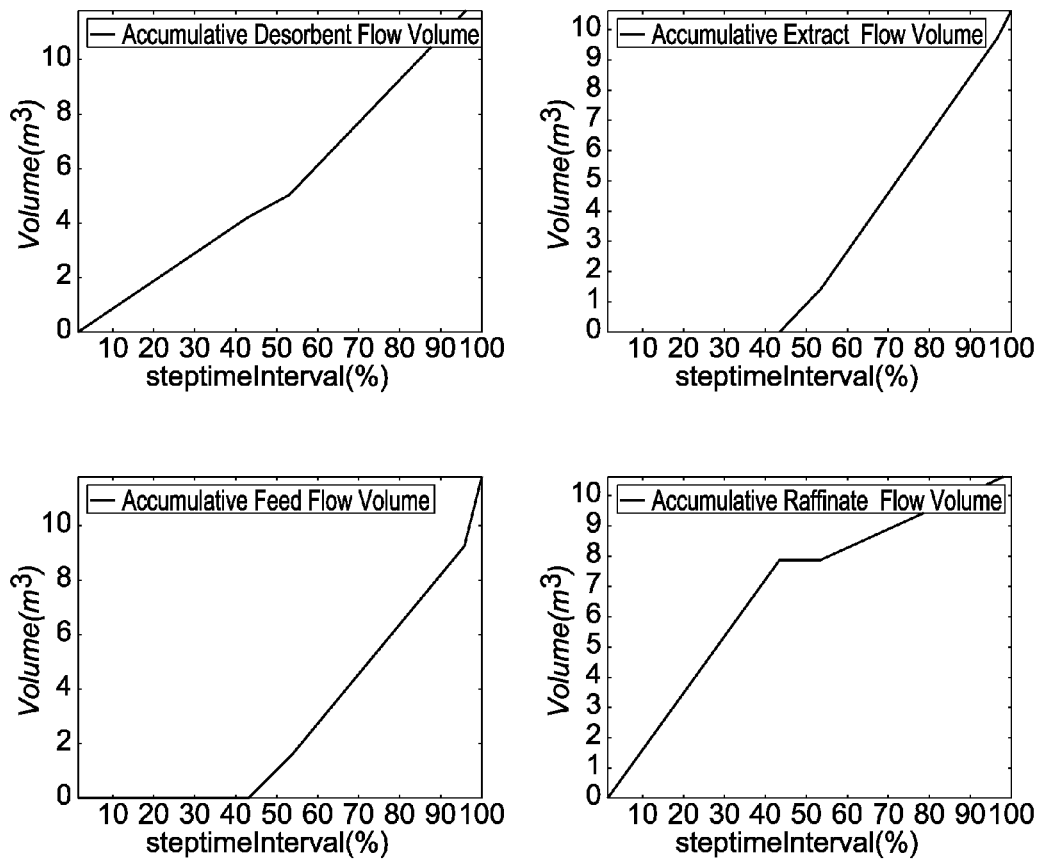
FIG. 3 shows plots of the accumulative flow volumes of streams during a step interval.

Example 1 is repeated, except that the flow rates of the feed stream, the raffinate stream, the desorbent stream and the extract stream are each varied during each step interval. Plots showing the flow rates of streams during each step interval are shown in FIG. 2. Plots showing the accumulative flow volumes of these streams during each step interval are shown in FIG. 3.

As shown in FIG. 2, flow rates are adjusted in four subintervals within the step interval of 2.83 minutes. The first subinterval extends from the beginning (time zero) to 1.23 minutes of the step interval, the second subinterval extends from the 1.23 minutes to 1.50 minutes of the step interval, the third subinterval extends from 1.50 minutes to 2.74 minutes of the step interval, and the fourth subinterval extends from 2.74 minutes to 2.83 minutes of the step interval.

As shown in FIG. 2, during the first subinterval (0 to 1.23 minutes), no feed is introduced (i.e., feed is introduced at a rate of zero m³/min). During the second subinterval (1.23 to 1.50 minutes), feed is introduced at a rate of 2.05 m³/min. During the third subinterval (1.50 to 2.74 minutes), feed is introduced at a rate of 2.41 m³/min. During the fourth and last subinterval (2.74 to 2.83 minutes), feed is introduced at a rate of 8.5 m³/min.

As shown in FIG. 2, during the first subinterval (0 to 1.23 minutes), raffinate is withdrawn at a rate of 3.58 m³/min During the second subinterval (1.23 to 1.50 minutes), raffinate is withdrawn at a rate of 0.00 m³/min. During the third subinterval (1.50 to 2.74 minutes), raffinate is withdrawn at a rate of 1.18 m³/min. During the fourth and last subinterval (2.74 to 2.83 minutes), raffinate is withdrawn at a rate of 0.00 m³/min.

As shown in FIG. 2, during the first subinterval (0 to 1.23 minutes), extract is withdrawn at a rate of 0.00 m³/min During the second subinterval (1.23 to 1.50 minutes), extract is withdrawn at a rate of 4.88 m³/min. During the third subinterval (1.50 to 2.74 minutes), extract is withdrawn at a rate of 6.77 m³/min During the fourth and last subinterval (2.74 to 2.83 minutes), extract is withdrawn at a rate of 8.50 m³/min.

As shown in FIG. 2, during the first subinterval (0 to 1.23 minutes), desorbent is introduced at a rate of 3.58 m³/min During the second subinterval (1.23 to 1.50 minutes), desorbent is introduced at a rate of 2.83 m³/min. During the third subinterval (1.50 to 2.74 minutes), desorbent is introduced at a rate of 5.53 m³/min. During the fourth and last subinterval (2.74 to 2.83 minutes), desorbent is introduced at a rate of 0.00 m³/min.

As shown in FIG. 2, the flow rate of circulating fluid through the buffer zone is also varied during the step interval. In particular, during the first subinterval (0 to 1.23 minutes), the flow rate of circulating fluid through the buffer zone is 0.0 m³/min During the second subinterval (1.23 to 1.50 minutes), the flow rate of circulating fluid through the buffer zone is 5.66 m³/min. During the third subinterval (1.50 to 2.74 minutes), the flow rate of circulating fluid through the buffer zone is 2.97 m³/min. During the fourth and last subinterval (2.74 to 2.83 minutes), the flow rate of circulating fluid through the buffer zone is 8.50 m³/min.

In the foregoing discussion of FIG. 2, flow rates are described in terms of four unequal subintervals. In the discussion of FIG. 3 below, the accumulative flow volumes are described in terms of different subintervals. In particular, five subintervals are described in connection with FIG. 3. These subintervals are equal and are each one-fifth (approximately 0.57 minutes) of the total step interval (2.83 minutes).

As shown in FIG. 3, (1) approximately 8% of the feed is introduced in the first, one-fifth subinterval (0 to 0.57 min); (2) approximately 11% of the feed is introduced in the second, one-fifth subinterval (0.57 to 1.13 min); (3) approximately 16% of the feed is introduced in the third, one-fifth subinterval (1.13 to 1.7 min); (4) approximately 24% of the feed is introduced in the fourth, one-fifth subinterval (1.7 to 2.26 min); and (5) approximately 41% of the feed is introduced in the fifth and final, one-fifth subinterval (2.26 to 2.83 min).

Also as shown in FIG. 3, (1) approximately 36% of the raffinate is withdrawn in the first, one-fifth subinterval (0 to 0.57 min), (2) approximately 36% of the raffinate is withdrawn in the second, one-fifth subinterval (0.57 to 1.13 min), (3) approximately 11% of the raffinate is withdrawn in the third, one-fifth subinterval (1.13 to 1.7 min), (4) approximately 11% of the raffinate is withdrawn in the fourth, one-fifth subinterval (1.7 to 2.26 min), and (5) approximately 6% of the raffinate is withdrawn in the fifth and final, one-fifth subinterval (2.26 to 2.83 min).

Also as shown in FIG. 3, (1) approximately 0% of the extract is withdrawn in the first, one-fifth subinterval (0 to 0.57 min), (2) approximately 0% of the extract is withdrawn in the second, one-fifth subinterval (0.57 to 1.13 min), (3) approximately 27% of the extract is withdrawn in the third, one-fifth subinterval (1.13 to 1.7 min), (4) approximately 35% of the extract is withdrawn in the fourth, one-fifth subinterval (1.7 to 2.26 min), and (5) approximately 38% of the extract is withdrawn in the fifth and final, one-fifth subinterval (2.26 to 2.83 min).

Also as shown in FIG. 3, (1) approximately 16% of the desorbent is introduced in the first, one-fifth subinterval (0 to 0.57 min), (2) approximately 17% of the desorbent is introduced in the second, one-fifth subinterval (0.57 to 1.13 min), (3) approximately 17% of the desorbent is introduced in the third, one-fifth subinterval (1.13 to 1.7 min), (4) approximately 25% of the desorbent is introduced in the fourth, one-fifth subinterval (1.7 to 2.26 min), and (5) approximately 25% of the desorbent is introduced in the fifth and final, one-fifth subinterval (2.26 to 2.83 min).

A separation of 1.54 m³/min of feed (0.00305 m³/min/kg-adsorbent) is achieved in Example 2 with a desorbent to feed ratio of 2.79. In Example 2, the achieved throughput is 3.36% higher than the throughput achieved in Comparative Example 1.

Example 3 (Comparative)

In this Example, the mass transfer coefficient, k, is 2 min$^{-1}$. The flow rates of the inlet and outlet streams are held constant over each step interval. Each step interval (i.e., the duration during which streams are introduced and withdrawn from the simulated moving-bed adsorptive apparatus between switching intervals) is 1.60 minutes.

During each step, 5.0 m³ of desorbent and 6.1 m³ of feed are introduced into the simulated moving-bed adsorptive apparatus, and 3.7 m³ of extract and 7.4 m³ of raffinate are withdrawn from the simulated moving-bed adsorptive apparatus.

A separation of 3.79 m³ feed/min (0.00752 m³ feed/min/kg-adsorbent) is achieved, with a desorbent to feed ratio of 0.825.

Example 4

Figure 4:
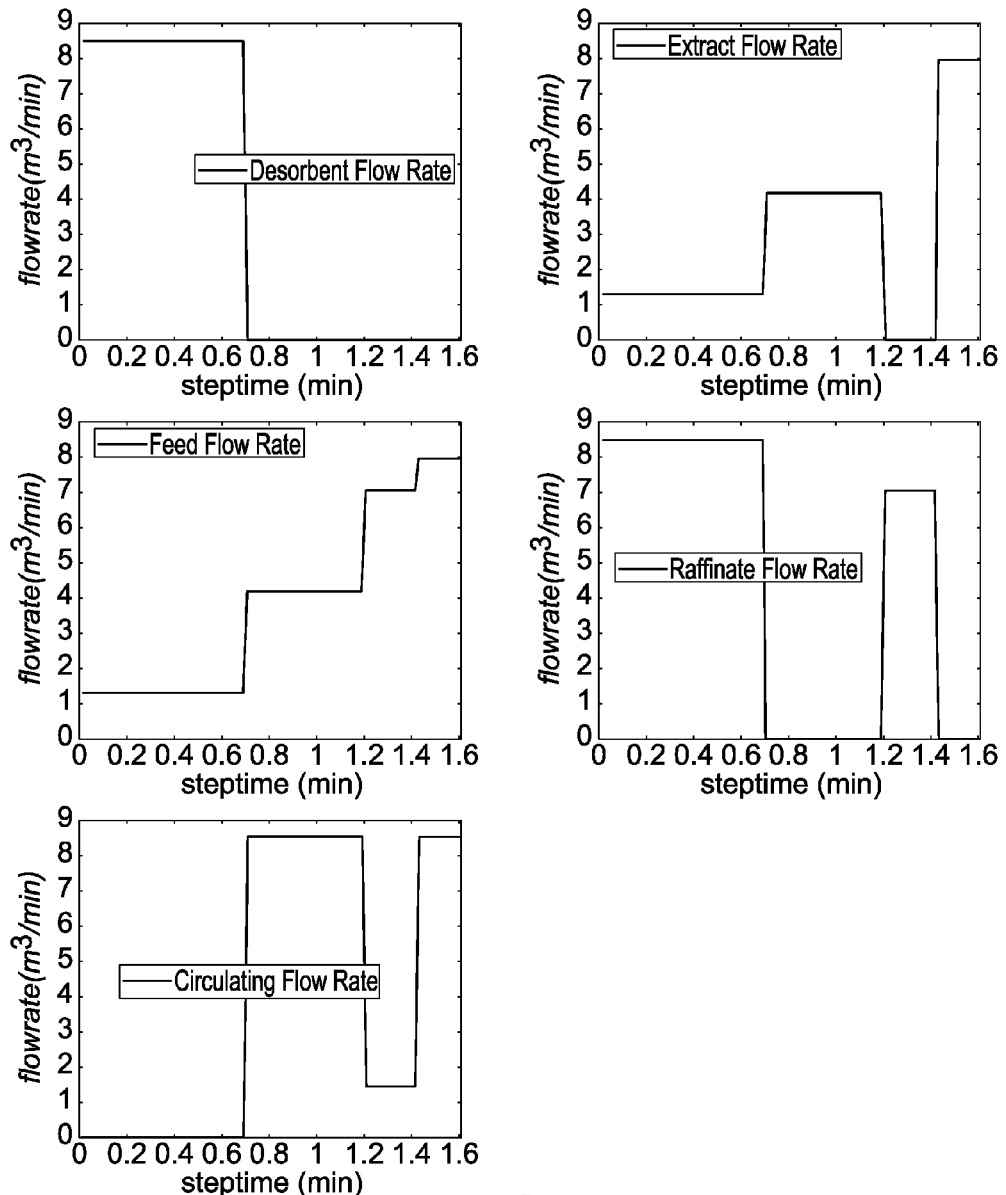
FIG. 4 shows plots of flow rates of streams during a step interval.
Figure 5:
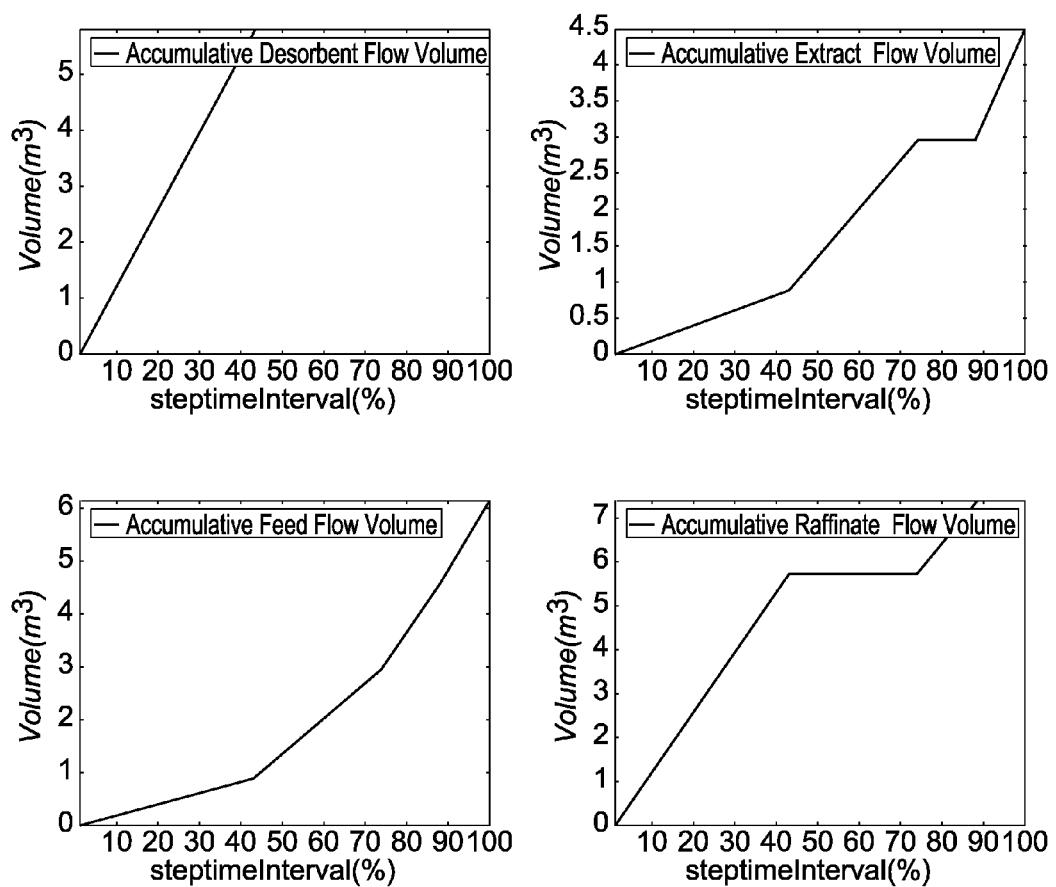
FIG. 5 shows plots of the accumulative flow volumes of streams during a step interval.

Example 3 is repeated, except that the flow rates of the feed stream, the raffinate stream, the desorbent stream and the extract stream are each varied during each step interval. Plots showing the flow rates of streams during each step interval are shown in FIG. 4. Plots showing the accumulative flow volumes of these streams during each step interval are shown in FIG. 5.

As shown in FIG. 4, flow rates are adjusted in four subintervals within the step interval of 1.61 minutes. The first subinterval extends from the beginning (time zero) to 0.69 minutes of the step interval, the second subinterval extends from the 0.69 minutes to 1.18 minutes of the step interval, the third subinterval extends from 1.18 minutes to 1.41 minutes of the step interval, and the fourth subinterval extends from 1.41 minutes to 1.61 minutes of the step interval.

As shown in FIG. 4, during the first subinterval (0 to 0.69 minutes), feed is introduced at a rate of 1.30 m³/min. During the second subinterval (0.69 to 1.18) minutes, feed is introduced at a rate of 4.18 m³/min During the third subinterval (1.18 to 1.41) minutes, feed is introduced at a rate of 7.06 m³/min. During the fourth and last subinterval (1.41 to 1.61) minutes, feed is introduced at a rate of 7.96 m³/min.

As shown in FIG. 4, during the first subinterval (0 to 0.69 minutes), raffinate is withdrawn at a rate of 8.49 m³/min During the second subinterval (0.69 to 1.18 minutes), raffinate is withdrawn at a rate of 0 m³/min. During the third subinterval (1.18 to 1.41 minutes), raffinate is withdrawn at a rate of 7.06 m³/min. During the fourth and last subinterval (1.41 to 1.61 minutes), raffinate is withdrawn at a rate of 0.00 m³/min.

As shown in FIG. 4, during the first subinterval (0 to 0.69 minutes), extract is withdrawn at a rate of 1.30 m³/min During the second subinterval (0.69 to 1.18 minutes), extract is withdrawn at a rate of 4.18 m³/min. During the third subinterval (1.18 to 1.41 minutes), extract is withdrawn at a rate of 0.00 m³/min During the fourth and last subinterval (1.41 to 1.61 minutes), extract is withdrawn at a rate of 7.96 m³/min.

As shown in FIG. 4, during the first subinterval (0 to 0.69 minutes), desorbent is introduced at a rate of 8.49 m³/min During the second subinterval (0.69 to 1.18 minutes), desorbent is introduced at a rate of 0.00 m³/min. During the third subinterval (1.18 to 1.41 minutes), desorbent is introduced at a rate of 0.00 m³/min. During the fourth and last subinterval (1.41 to 1.61 minutes), desorbent is introduced at a rate of 0.00 m³/min.

As shown in FIG. 4, the flow rate of circulating fluid through the buffer zone is also varied during the step interval. In particular, during the first subinterval (0 to 0.69 minutes), the flow rate of circulating fluid through the buffer zone is 0.01 m³/min. During the second subinterval (0.69 to 1.18 minutes), the flow rate of circulating fluid through the buffer zone is 8.50 m³/min. During the third subinterval (1.18 to 1.41 minutes), the flow rate of circulating fluid through the buffer zone is 1.44 m³/min. During the fourth and last subinterval (1.41 to 1.61 minutes), the flow rate of circulating fluid through the buffer zone is 8.50 m³/min.

In the foregoing discussion of FIG. 4, flow rates are described in terms of four unequal subintervals. In the discussion of FIG. 5 below, the accumulative flow volumes are described in terms of different subintervals. In particular, five subintervals are described in connection with FIG. 5. These subintervals are equal and are each one-fifth (0.32 minutes) of the total step interval (1.6 minutes).

As shown in FIG. 5, (1) approximately 8% of the feed is introduced in the first, one-fifth subinterval (0 to 0.32 min), (2) approximately 11% of the feed is introduced in the second, one-fifth subinterval (0.32 to 0.64 min), (3) approximately 16% of the feed is introduced in the third, one-fifth subinterval (0.64 to 0.96 min), (4) approximately 24% of the feed is introduced in the fourth, one-fifth subinterval (0.96 to 1.28 min), and (5) approximately 41% of the feed is introduced in the fifth and final, one-fifth subinterval (1.28 to 1.6 min).

Also as shown in FIG. 5, (1) approximately 34% of the raffinate is withdrawn in the first, one-fifth subinterval (0 to 0.32 min), (2) approximately 36% of the raffinate is withdrawn in the second, one-fifth subinterval (0.32 to 0.64 min), (3) approximately 10% of the raffinate is withdrawn in the third, one-fifth subinterval (0.64 to 0.96 min), (4) approximately 5% of the raffinate is withdrawn in the fourth, one-fifth subinterval (0.96 to 1.28 min), and (5) approximately 15% of the raffinate is withdrawn in the fifth and final, one-fifth subinterval (1.28 to 1.6 min).

Also as shown in FIG. 5, (1) approximately 9% of the extract is withdrawn in the first, one-fifth subinterval (0 to 0.32 min), (2) approximately 9% of the extract is withdrawn in the second, one-fifth subinterval (0.32 to 0.64 min), (3) approximately 24% of the extract is withdrawn in the third, one-fifth subinterval (0.64 to 0.96 min), (4) approximately 24% of the extract is withdrawn in the fourth, one-fifth subinterval (0.96 to 1.28 min), and (5) approximately 34% of the extract is withdrawn in the fifth and final, one-fifth subinterval (1.28 to 1.6 min).

Also as shown in FIG. 5, (1) approximately 43% of the desorbent is introduced in the first, one-fifth subinterval (0 to 0.32 min), (2) approximately 43% of the desorbent is introduced in the second, one-fifth subinterval (0.32 to 0.64 min), (3) approximately 14% of the desorbent is introduced in the third, one-fifth subinterval (0.64 to 0.96 min), (4) 0% of the desorbent is introduced in the fourth, one-fifth subinterval (0.96 to 1.28 min), and (5) 0% of the desorbent is introduced in the fifth and final, one-fifth subinterval (1.28 to 1.6 min).

A separation of 3.82 m³/min of feed (0.00758 m³/min/kg-adsorbent) is achieved in Example 4 with a desorbent to feed ratio of 0.96. In Example 4, the achieved throughput is 0.79% higher than the throughput achieved in Comparative Example 3.

Parameters for Examples 5 and 6

In Examples 5-6 which follow, an SMB model that consists of 8-24 beds is employed. A mixture of xylenes (paraxylene (PX), orthoxylene (OX), metaxylene (MX), and ethylbenzene (EB)) and desorbent (para-diethyl benzene (pDEB)) was assumed to be fed to the unit.

The zone configuration is consistent in this study. For an SMB with 24 beds, the zone configuration is fixed to 6:9:6:3 (i.e. six beds between desorbent and extract, nine beds between extract and feed, six beds between feed and raffinate, and three bed between raffinate and desorbent). For SMBs with fewer numbers of beds, the ratio is kept as close as possible to 2:3:2:1; for example, for an SMB with 16 beds, the zone configuration is 4:6:4:2.

Consistent with M. Minceva, and A. E. Rodrigues, 'Modeling and Simulation of a Simulated Moving Bed for the Separation of P-Xylene', *Industrial & Engineering Chemistry Research*, 41 (2002), 3454-61, the following assumptions are made: (1) isothermal, isobaric operation; (2) constant velocity within each zone; (3) solid phase concentration is homogeneous throughout adsorbent particles; and (4) the mass transfer between the liquid and adsorbent phases is described by the linear driving force (LDF) model.

Based on these assumptions, mass balance equations can be written as:

$$\frac{\partial C_{ik}(z,t)}{\partial t} = \mathcal{D}_{Lk}(t)\frac{\partial^2 C_{ik}(z,t)}{\partial z^2} - v_k^*(t)\frac{\partial C_{ik}(z,t)}{\partial z} - \frac{(1-\varepsilon)}{\varepsilon}\frac{\partial q_{ik}(z,t)}{\partial t}$$

where i is the index for components (i=PX, MX, OX, EB, PDEB); k is the index for columns (k=1 ... $N_{bed}$, where $N_{bed}$ is the total number of beds); C is the bulk liquid concentration $$\left(\text{unit } \frac{\text{kg}}{\text{m}^3}\right);$$

q is the adsorbate concentration $$\left(\text{unit } \frac{\text{kg}}{\text{m}^3}\right);$$

$\varepsilon$ is the overall porosity; $\mathcal{D}$ is the axial dispersion coefficient; and $v_k^*$ is the interstitial velocity in columns.

This mass balance equation describes the change of bulk liquid concentration at a specific position inside of a column (first term) with respect to dispersion (second term), convection (third term), and adsorption/desorption process (fourth term).

The LDF model is written as:

$$\frac{\partial q_{ik}(z,t)}{\partial t} = k(q_{ik}^*(z,t) - q_{ik}(z,t))$$

where q* is the adsorbate concentration in equilibrium with the liquid phase $$\left(\text{unit } \frac{\text{kg}}{\text{m}^3}\right).$$

The LDF model describes the mass flux into the solid phase. The adsorbate concentration in equilibrium with the liquid phase can be obtained from an adsorption isotherm.

At the node between columns, the mass balance is calculated by subtracting outlet flow rates and adding inlet flow rates:

$$F_{k+1} = F_k + F_{Feed,k} + F_{desorbent,k} - F_{raffinate,k} - F_{extract,k}$$

For columns that are not connected to inlet or outlet streams, $F_{Feed,k}$ or $F_{desorbent,k}$ or $F_{raffinate,k}$ or $F_{extract,k}$ is zero.

The CSS constraints are given as:

$$C_{k+1}(z,t_{end}) = C_k(z,t_0)$$

where $t_{end}$ is the time at the end of a step, and $t_0$ is the beginning of a step. Here, stepwise symmetry is assumed, where every step is identical.

Model parameters were taken from the literature, in particular, from M. Minceva, and A. E. Rodrigues, 'Modeling and Simulation of a Simulated Moving Bed for the Separation of P-Xylene', *Industrial & Engineering Chemistry Research*, 41 (2002), 3454-61. Model parameters are summarized in Table 1.

TABLE 1

| SMB unit geometry | model parameter |
|---|---|
| $L_c$ = 113.5 cm | Pe = $v_k L_k/D_{Lk}$ = 2000 |
| $d_c$ = 411.7 cm | k = 2 min$^{-1}$ |
| $V_c$ = 15.1 × 10$^6$ cm$^3$ | $d_p$ = 0.092 cm |
| no. of columns = 24 | $\varepsilon$ = 0.39 |
| configuration = 6-9-6-3 | $\rho$ = 1.39 g/cm$^3$ |
| | $q_{mPX(MX, OX, EB)}$ = 130.3 mg/g |
| | $K_{PX}$ = 1.0658 cm$^3$/mg |
| | $K_{MX}$ = 0.2299 cm$^3$/mg |
| | $K_{OX}$ = 0.1884 cm$^3$/mg |
| | $K_{EB}$ = 0.3067 cm$^3$/mg |
| | $q_{mPDEB}$ = 107.7 mg/g |
| | $K_{PDEB}$ = 1.2935 cm$^3$/mg |

The mass transfer coefficient was changed from 2 min$^d$ to 0.75 min$^d$.

The optimization problem was formulated as follows:
Objective function: maximize $F_{Feed}$
Decision variables: $F_1$, $F_2$, $F_3$, $F_4$, $t_{st}$
where $F_j$'s are zone flow rates, and $t_{st}$ is the step time
Main Constraint: Extract purity (PX)≥99.7%
Extract recovery (PX)≥97.0%

The model was discretized into a set of algebraic differential equations by applying the center finite difference method (CFDM) to the spatial domain and orthogonal collocation finite element method (OCFEM) to the temporal domain respectively. The discretized problem was solved by an interior-point optimization algorithm, IPOPT.

Example 5

This Example involves a reduction in the number of adsorbent beds with constant total sieve for paraxylene separation from mixed xylenes.

In this first scenario, a reduced number of beds were used, each with a larger volume to maintain a constant amount of adsorbent. For example, in one case study, the number of beds was reduced from 24 to 8, and the length of each bed was increased from 1.135 m to 3.405 m. In this scenario, the total amount of adsorbent for all cases is fixed.

The results of model-based SMB optimization are shown in Tables 2 and 3. Table 2 shows the optimized flow rates.

TABLE 2

| # of Beds | 8 | 16 | 24 |
|---|---|---|---|
| Substep 1 length (min) | 2.90 | 1.21 | 0.67 |
| Substep 2 length (min) | 3.25 | 1.69 | 1.24 |
| Substep 1 feed flow rate (m$^3$/min) | 0.00 | 0.00 | 0.00 |
| Substep 2 feed flow rate (m$^3$/min) | 4.29 | 4.03 | 3.62 |
| Substep 1 extract flow rate (m$^3$/min) | 0.00 | 0.00 | 0.00 |
| Substep 2 extract flow rate (m$^3$/min) | 6.77 | 6.49 | 6.20 |
| Substep 1 desorbent flow rate (m$^3$/min) | 5.85 | 6.32 | 6.97 |
| Substep 2 desorbent flow rate (m$^3$/min) | 3.65 | 3.41 | 3.67 |
| Substep 1 raffinate flow rate (m$^3$/min) | 5.85 | 6.32 | 6.97 |
| Substep 2 raffinate flow rate (m$^3$/min) | 1.18 | 0.96 | 1.08 |

TABLE 2-continued

| # of Beds | 8 | 16 | 24 |
|---|---|---|---|
| Substep 1 zone 1 flow rate (m³/min) | 5.85 | 6.51 | 6.97 |
| Substep 2 zone 1 flow rate (m³/min) | 8.50 | 8.50 | 8.50 |

Table 3 shows that the PowerFeed strategy effectively mitigates the performance deterioration associated with fewer numbers of beds.

TABLE 3

| # of Beds | Production without PowerFeed (m³/min) | Production with PowerFeed (m³/min) | Losses with reduced beds (Without PowerFeed) | Losses with reduced beds (With PowerFeed) |
|---|---|---|---|---|
| 8 | 1.95 | 2.26 | 14% | 4% |
| 16 | 2.22 | 2.35 | 2% | 0% |
| 24 | 2.28 | 2.35 | — | — |

Using 24 beds without PowerFeed, a maximum feed flow rate of 2.28 m³/min is achieved. When the number of beds was reduced from 24 to 8, the maximum feed flow rate was reduced from 2.28 to 1.95 m³/min (16.5% loss). On the other hand, using 24 beds and PowerFeed, a maximum feed flow rate of 2.34 m³/min is achieved. When the number of beds was reduced from 24 to 8 and PowerFeed was used, the maximum feed flow rate remained a relatively high value of 2.26 m³/min. This result shows that a similar throughput can be achieved using 8 beds instead of 24 if the PowerFeed strategy is implemented. Additionally, the throughput can be pushed higher by 3% by using 24 beds and the PowerFeed strategy.

Example 6

This Example involves a reduction in the number of adsorbent beds with constant sieve per bed for paraxylene separation from mixed xylenes.

In a second scenario, a reduced number of beds were used, and each bed was held constant at 1.135 m long. In both scenarios, the PX purity in the extract was fixed to be 99.7%, and the PX recovery in the extract was fixed to be 97.0%. The optimization objective was to maximize the feed flow rate, which represents productivity. The optimized flow rates are shown in Table 4.

Note that case studies 12a and 12b both represent a system with 12 beds, but have different zone configurations: Case 12a has a zone configuration of 3:5:3:1 and case 12b has a zone configuration of 3:4:3:2. This is because an SMB with 12 beds cannot have a zone configuration of 2:3:2:1.

TABLE 4

| # of Beds | 8 | 12 | 12 | 16 | 24 |
|---|---|---|---|---|---|
| Case | 8 | 12a | 12b | 16 | 24 |
| Substep 1 length (min) | 3.13 | 2.06 | 2.45 | 1.49 | 0.67 |
| Substep 2 length (min) | 2.13 | 1.56 | 1.63 | 1.35 | 1.24 |
| Substep 1 flow rate (m³/min) | 0.00 | 0.00 | 0.00 | 0.00 | 0.00 |
| Substep 2 flow rate (m³/min) | 2.04 | 2.80 | 2.84 | 3.35 | 3.62 |
| Substep 1 extract flow rate (m³/min) | 0.00 | 0.00 | 0.00 | 0.00 | 0.00 |
| Substep 2 extract flow rate (m³/min) | 8.05 | 7.85 | 7.85 | 7.43 | 6.20 |
| Substep 1 desorbent flow rate (m³/min) | 2.10 | 3.16 | 2.65 | 4.08 | 6.97 |
| Substep 2 desorbent flow rate (m³/min) | 6.06 | 5.48 | 5.05 | 8.50 | 3.67 |
| Substep 1 raffinate flow rate (m³/min) | 2.10 | 3.16 | 2.65 | 3.76 | 6.97 |
| Substep 2 raffinate flow rate (m³/min) | 0.05 | 0.44 | 0.04 | 0.35 | 1.08 |
| Substep 1 zone 1 flow rate (m³/min) | 2.10 | 3.16 | 2.65 | 4.08 | 6.97 |
| Substep 2 zone 1 flow rate (m³/min) | 8.50 | 8.50 | 8.50 | 8.50 | 8.50 |

Table 5 shows the model-based SMB optimization results for scenario two.

TABLE 5

| # of Beds | Case | Production without PowerFeed (m³/min) | Production with PowerFeed (m³/min) | Losses with reduced beds (Without PowerFeed) | Losses with reduced beds (With PowerFeed) |
|---|---|---|---|---|---|
| 8 | 8 | 0.63 | 0.75 | 72% | 68% |
| 12 | 12a | 1.10 | 1.21 | 52% | 48% |
| 12 | 12b | 1.01 | 1.14 | 55% | 52% |
| 16 | 16 | 1.48 | 1.58 | 35% | 33% |
| 24 | 24 | 2.28 | 2.35 | — | — |

The decrease in maximum feed flow rate was large as the number of beds was reduced. In this scenario, the length of each bed was fixed to be 1.135 m, and fewer number of beds means a smaller amount of total adsorbent in the SMB. If the amount of adsorbent is reduced, then the volume of xylenes that can be successfully separated is reduced. When the number of beds was reduced from 24 to 8 without PowerFeed, the maximum feed flow rate was reduced dramatically from 2.28 to 0.63 m³/min. When the PowerFeed strategy is used, the maximum feed flow rate is consistently increased by about 0.10 m³/min Even when 8 beds are used, the maximum feed flow rate is increased from 0.63 to 0.75 m³/min, which is about 15% improvement using the PowerFeed strategy.

TABLE 6

| # of Beds | Case | Normalized Throughput without powerfeed (kg-feed/kg-sieve/hr) | Normalized Throughput with powerfeed (kg-feed/kg-sieve/hr) | Losses with reduced beds (Without PowerFeed) | Losses with reduced beds (With PowerFeed) |
|---|---|---|---|---|---|
| 8 | 8 | 0.284 | 0.339 | 17% | 3.9% |
| 12 | 12a | 0.331 | 0.363 | 3% | −3.0% |
| 12 | 12b | 0.305 | 0.341 | 11% | 3.2% |
| 16 | 16 | 0.333 | 0.356 | 3% | −1.0% |
| 24 | 24 | 0.342 | 0.353 | — | — |

The results for scenario two were compared on a per-bed basis (Table 6) to study the adsorbent efficiency. This was done by calculating the normalized feed flow rate (dividing the maximum feed flow rate by the number of beds, $F_{feed}/N_{bed}$) in each case. As shown in Table 5, the normalized feed flow rate without PowerFeed decreased by 17.0% as the number of beds decreased from 24 to 8, indicating the adsorbent is less efficient in the 8-bed system. With the implementation of PowerFeed the decrease in normalized feed flow rate was less than 3.9%, indicating that the PowerFeed strategy increases adsorbent efficiency compared to the conventional, constant-flow alternative. The results in Table 6 also show that an SMB with the zone configuration used in case 12a has the maximum normalized feed flow rate—even surpassing that of the 24-bed SMB with PowerFeed.

Example 7

This Example involves a reduction in the number of adsorbent beds for ethylbenzene extraction from m-xylene and o-xylene.

The same model (with isotherm parameters taken from Silva et al. *Chemical Engineering & Technology*, 37 (2014) 1541-1551 in this case) was used to explore the impact of PowerFeed on throughput for EB extraction from the raffinate stream (18% EB, 65% MX 1% PX and 16% OX) from the examples above. SMBs with 16 beds and 24 beds were studied, where the amount of sieve per bed was held constant (similar to Example 6). The EB purity in the extract was constrained to 80% and the recovery was also constrained to 80%.

Results are shown in Table 7.

TABLE 7

| # of Columns | Case | Normalized Throughput without PowerFeed (kg-feed/kg-sieve/hr) | Normalized Throughput with PowerFeed (kg-feed/kg-sieve/hr) |
| --- | --- | --- | --- |
| 8 | 8 | 0.284 | 0.339 |
| 12 | 12a | 0.331 | 0.363 |
| 12 | 12b | 0.305 | 0.341 |
| 16 | 16 | 0.333 | 0.356 |
| 24 | 24 | 0.342 | 0.353 |

As is seen in this example, a higher improvement (based on total throughput) from non-PowerFeed to 2-substep PowerFeed is shown with a lower number of beds. It stands to reason that less beds are required to meet similar performance objectives when the PowerFeed is applied in this EB extraction case.

Example 8

The same model (with isotherm parameters taken from Silva et al. *Chemical Engineering & Technology*, 37 (2014) 1541-1551 in this case) was used to explore the impact of PowerFeed on product purity. In this case, an SMB with 24 beds was studied with each bed being 1.135 meters in length. The operating conditions were constrained to an average feed rate of 2.25 m3/min, the desorbent to feed ratio was constrained to 1.83 and the product recovery was constrained to 97.0%. This unit was optimized to determine the highest possible product purity in a non-powerfeed scenario. The unit was then optimized to determine the highest possible product purity with PowerFeed implemented as two substeps in which all flows were allowed to change. The run conditions for the non PowerFeed Case and the PowerFeed case are shown in Table 8.

TABLE 8

| | Non PowerFeed | With PowerFeed |
| --- | --- | --- |
| Substep 1 length (min) | 0.98 | 1.15 |
| Substep 2 length (min) | 0.98 | 0.90 |
| Substep 1 feed flow rate (m$^3$/min) | 2.25 | 0.00 |
| Substep 2 feed flow rate (m$^3$/min) | 2.25 | 5.13 |
| Substep 1 extract flow rate (m$^3$/min) | 3.24 | 0.00 |
| Substep 2 extract flow rate (m$^3$/min) | 3.24 | 7.34 |
| Substep 1 desorbent flow rate (m$^3$/min) | 4.12 | 4.69 |
| Substep 2 desorbent flow rate (m$^3$/min) | 4.12 | 3.40 |
| Substep 1 raffinate flow rate (m$^3$/min) | 3.14 | 4.69 |
| Substep 2 raffinate flow rate (m$^3$/min) | 3.14 | 1.19 |
| Substep 1 zone 1 flow rate (m$^3$/min) | 7.07 | 5.91 |
| Substep 2 zone 1 flow rate (m$^3$/min) | 7.07 | 8.50 |

TABLE 9

| | Non PowerFeed | With PowerFeed | Percent Increase |
| --- | --- | --- | --- |
| Average Feed Rate (m$^3$/min) | 2.25 | 2.25 | 0.00% |
| Product Purity (%) | 99.70 | 99.86 | 0.16% |
| Product Recovery (%) | 97.00 | 97.00 | 0.00% |
| Desorbent/Feed Ratio | 1.83 | 1.83 | 0.00% |

As seen in this example, the results in Table 9 show that the implementation of PowerFeed can increase product purity by 0.16%.

Example 9

The same model (with isotherm parameters taken from Silva et al. *Chemical Engineering & Technology*, 37 (2014) 1541-1551 in this case) was used to explore the impact of PowerFeed on desorbent usage. In this case, an SMB with 24 beds was studied with each bed being 1.135 meters in length. The operating conditions were constrained to an average feed rate of 2.25 m3/min and the product purity was constrained to 99.7%. This unit was optimized to determine the minimum required desorbent to feed ratio in a non-powerfeed scenario. The unit was then optimized to determine the minimum required desorbent to feed ratio with PowerFeed implemented as two substeps in which all flows were allowed to change. The run conditions for the non PowerFeed Case and the PowerFeed case are shown in Table 10.

TABLE 10

| | Non PowerFeed | With PowerFeed |
| --- | --- | --- |
| Substep 1 length (min) | 0.98 | 1.30 |
| Substep 2 length (min) | 0.98 | 0.77 |
| Substep 1 feed flow rate (m$^3$/min) | 2.25 | 0.00 |
| Substep 2 feed flow rate (m$^3$/min) | 2.25 | 6.02 |
| Substep 1 extract flow rate (m$^3$/min) | 3.24 | 0.00 |
| Substep 2 extract flow rate (m$^3$/min) | 3.24 | 5.96 |
| Substep 1 desorbent flow rate (m$^3$/min) | 4.12 | 4.64 |
| Substep 2 desorbent flow rate (m$^3$/min) | 4.12 | 0.00 |
| Substep 1 raffinate flow rate (m$^3$/min) | 3.14 | 4.64 |
| Substep 2 raffinate flow rate (m$^3$/min) | 3.14 | 0.06 |
| Substep 1 zone 1 flow rate (m$^3$/min) | 7.07 | 5.91 |
| Substep 2 zone 1 flow rate (m$^3$/min) | 7.07 | 8.50 |

TABLE 11

| | Non PowerFeed | With PowerFeed | Percent Increase |
| --- | --- | --- | --- |
| Average Feed Rate (m$^3$/min) | 2.25 | 2.25 | 0.00% |
| Product Purity (%) | 99.70 | 99.70 | 0.00% |
| Product Recovery (%) | 97.00 | 97.00 | 0.00% |
| Desorbent/Feed Ratio | 1.83 | 1.30 | −29.18% |

As seen in this example, the results in Table 11 show that the implementation of PowerFeed can decrease the amount of desorbent used by 29.18%.

Example 10

The same model (with isotherm parameters taken from Silva et al. *Chemical Engineering & Technology*, 37 (2014) 1541-1551 in this case) was used to explore the impact of PowerFeed on product recovery. In this case, an SMB with 24 beds was studied with each bed being 1.135 meters in length. The operating conditions were constrained to an average feed rate of 2.25 m3/min, the product purity was constrained to 99.7% and the desorbent to feed ratio was constrained to 1.83. This unit was optimized to determine the maximum product recovery in a non-powerfeed scenario. The unit was then optimized to determine the maximum product recovery with PowerFeed implemented as two substeps in which all flows were allowed to change. The run conditions for the non PowerFeed Case and the PowerFeed case are shown in Table 12.

TABLE 12

|  | Non PowerFeed | With PowerFeed |
| --- | --- | --- |
| Substep 1 length (min) | 0.98 | 1.16 |
| Substep 2 length (min) | 0.98 | 0.80 |
| Substep 1 feed flow rate (m$^3$/min) | 2.25 | 0.00 |
| Substep 2 feed flow rate (m$^3$/min) | 2.25 | 5.48 |
| Substep 1 extract flow rate (m$^3$/min) | 3.24 | 0.00 |
| Substep 2 extract flow rate (m$^3$/min) | 3.24 | 7.93 |
| Substep 1 desorbent flow rate (m$^3$/min) | 4.12 | 4.53 |
| Substep 2 desorbent flow rate (m$^3$/min) | 4.12 | 3.54 |
| Substep 1 raffinate flow rate (m$^3$/min) | 3.14 | 4.53 |
| Substep 2 raffinate flow rate (m$^3$/min) | 3.14 | 1.09 |
| Substep 1 zone 1 flow rate (m$^3$/min) | 7.07 | 5.91 |
| Substep 2 zone 1 flow rate (m$^3$/min) | 7.07 | 8.50 |

TABLE 13

|  | Non PowerFeed | With PowerFeed | Percent Increase |
| --- | --- | --- | --- |
| Average Feed Rate (m$^3$/min) | 2.25 | 2.25 | 0.00% |
| Product Purity (%) | 99.70 | 99.70 | 0.00% |
| Product Recovery (%) | 97.00 | 97.40 | 0.41% |
| Desorbent/Feed Ratio | 1.83 | 1.83 | 0.00% |

As see in this example, the results in Table 13 show that the implementation of PowerFeed can increase product recovery by 0.41%.

What is claimed is:

1. A process for separating at least one C8 aromatic from a mixture of at least two C8 aromatics by simulated moving-bed adsorptive separation, said process comprising the steps of:
    (a) introducing a feed stream, which comprises at least two C8 aromatics, into a simulated moving-bed adsorptive apparatus, wherein said simulated moving-bed adsorptive apparatus comprises multiple beds containing adsorbent material;
    (b) introducing a desorbent stream, which comprises desorbent, into the simulated moving-bed adsorptive apparatus;
    (c) withdrawing an extract stream, which comprises desorbent and at least one C8 aromatic, from the simulated moving-bed adsorptive apparatus;
    (d) withdrawing at least one raffinate stream, which comprises at least one C8 aromatic, which is different from the C8 aromatic in the extract stream of step (c), from the simulated moving-bed adsorptive apparatus;
    (e) maintaining a flow of circulating fluid throughout the simulated moving-bed adsorptive apparatus; and
    (f) switching the flow of streams into and out of the simulated moving-bed adsorptive apparatus to a bed downstream in terms of the direction of the circulating fluid at set time interval X,
    wherein the rate flow of feed introduced in step (a) is varied during time interval X.

2. The process of claim 1, wherein the mixture of at least two C8 aromatics comprises paraxylene, orthoxylene, metaxylene and ethylbenzene, and
    wherein the extract stream of step (c) comprises paraxylene.

3. The process of claim 1, wherein the mixture of at least two C8 aromatics comprises orthoxylene, metaxylene and ethylbenzene, and
    wherein the extract stream of step (c) comprises ethylbenzene.

4. The process of claim 2, wherein a single raffinate stream is withdrawn from the simulated moving-bed adsorptive apparatus.

5. The process of claim 2, wherein more of the at least one multicomponent feed is introduced into the simulated moving-bed adsorptive apparatus during the latter portion of time interval X than in the earlier portion of time interval X.

6. The process of claim 5, wherein less than 30% of the at least one multicomponent feed is introduced into the simulated moving-bed adsorptive apparatus during a time subinterval of from 0 to 40% of X,
    wherein at least 70% of the at least one multicomponent feed is introduced into the simulated moving-bed adsorptive apparatus during a time subinterval of from 40 to 100% of X.

7. The process of claim 5, wherein less than 10% of the feed, which is introduced in time interval X, is introduced during a time subinterval of from 0 to 20% of X,
    wherein less than 15% of the feed, which is introduced in time interval X, is introduced during a time subinterval of from 20 to 40% of X,
    wherein at least 15% of the feed, which is introduced in time interval X, is introduced during a time subinterval of from 40 to 60% of X,
    wherein at least 20% of the feed, which is introduced in time interval X, is introduced during a time subinterval of from 60 to 80% of X, and
    wherein at least 20% of the feed, which is introduced in time interval X, is introduced during a time subinterval of from 80 to 100% of X.

8. The process of claim 5, wherein less of the raffinate stream is withdrawn from the simulated moving-bed adsorptive apparatus during the latter portion of time interval X than in the earlier portion of time interval X.

9. The process of claim 8, wherein at least 60% of the raffinate stream is withdrawn from the simulated moving-bed adsorptive apparatus during a time subinterval of from 0 to 40% of X,
    wherein less than 40% of the raffinate stream is withdrawn from the simulated moving-bed adsorptive apparatus during a time subinterval of from 40 to 100% of X.

10. The process of claim 8, wherein at least 25% of the raffinate stream, which is withdrawn in time interval X, is withdrawn during a time subinterval of from 0 to 20% of X, wherein at least 25% of the raffinate stream, which is withdrawn in time interval X, is withdrawn during a time subinterval of from 20 to 40% of X, wherein less than 15% of the raffinate stream, which is withdrawn in time interval X, is withdrawn during a time subinterval of from 40 to 60% of X, wherein less than 15% of the raffinate stream, which is withdrawn in time interval X, is withdrawn during a time subinterval of from 60 to 80% of X, and wherein less than 20% of the raffinate stream, which is withdrawn in time interval X, is withdrawn during a time subinterval of from 80 to 100% of X.

11. The process of claim 2, wherein more of the extract stream is withdrawn from the simulated moving-bed adsorptive apparatus during the latter portion of time interval X than in the earlier portion of time interval X.

12. The process of claim 11, wherein less than 30% of the extract stream is withdrawn from the simulated moving-bed adsorptive apparatus during a time subinterval of from 0 to 40% of X, wherein at least 70% of the extract stream is withdrawn from the simulated moving-bed adsorptive apparatus during a time subinterval of from 40 to 100% of X.

13. The process of claim 12, wherein less than 15% of the extract stream, which is withdrawn in time interval X, is withdrawn during a time subinterval of from 0 to 20% of X, wherein less than 15% of the extract stream, which is withdrawn in time interval X, is withdrawn during a time subinterval of from 20 to 40% of X, wherein at least 15% of the extract stream, which is withdrawn in time interval X, is withdrawn during a time subinterval of from 40 to 60% of X, wherein at least 20% of the extract stream, which is withdrawn in time interval X, is withdrawn during a time subinterval of from 60 to 80% of X, and wherein at least 20% of the extract stream, which is withdrawn in time interval X, is withdrawn during a time subinterval of from 80 to 100% of X.

14. The process of claim 1, wherein at least two raffinate streams are withdrawn from the simulated moving-bed adsorptive apparatus, wherein a first raffinate stream comprises ethylbenzene and desorbent, and wherein a second raffinate stream comprises orthoxylene, metaxylene and desorbent.

15. The process any one of claim 1, wherein the at least one multicomponent feed further comprises n-nonane, wherein three raffinate streams are withdrawn from the simulated moving-bed adsorptive apparatus, wherein a first raffinate stream comprises ethylbenzene and desorbent, wherein a second raffinate stream comprises orthoxylene, metaxylene and desorbent, and wherein a third raffinate stream comprises n-nonane and desorbent.

16. The process of claim 4, wherein the extract stream from step (c) is passed to a first distillation zone to separate paraxylene from desorbent, wherein the raffinate stream is passed to a second distillation zone to separate ethylbenzene, orthoxylene and metaxylene from desorbent.

17. The process of claim 14, wherein the extract stream from step (c) is passed to a first distillation zone to separate paraxylene from desorbent, wherein the first raffinate stream is passed to a second distillation zone to separate ethylbenzene from desorbent, and wherein the second raffinate stream is passed to a third distillation zone to separate orthoxylene and metaxylene from desorbent.

18. The process of claim 15, wherein the extract stream from step (c) is passed to a first distillation zone to separate paraxylene from desorbent, wherein the first raffinate stream is passed to a second distillation zone to separate ethylbenzene from desorbent, wherein the second raffinate stream is passed to a third distillation zone to separate orthoxylene and metaxylene from desorbent, and wherein the third raffinate stream is passed to a fourth distillation zone to separate n-nonane from desorbent.

19. The process of claim 16, wherein ethylbenzene, orthoxylene and metaxylene, which is separated from desorbent in the second distillation zone, is passed to a liquid phase isomerization zone, a vapor phase isomerization zone, or a combination thereof, to produce a product stream comprising paraxylene, orthoxylene and metaxylene.

20. The process of claim 17, wherein ethylbenzene, which is separated from desorbent in the second distillation zone, is passed to a vapor phase isomerization zone to produce a product stream comprising paraxylene, orthoxylene and metaxylene or a product stream comprising benzene and ethylene, and wherein orthoxylene and metaxylene, which is separated from desorbent in the third distillation zone, is passed to a liquid phase isomerization zone to produce a product stream comprising paraxylene, orthoxylene and metaxylene.

21. A process for separating at least one C8 aromatic from a mixture of at least two C8 aromatics by simulated moving-bed adsorptive separation, said process comprising the steps of:

(a) introducing a feed stream, which comprises at least two C8 aromatics, into a simulated moving-bed adsorptive apparatus, wherein said simulated moving-bed adsorptive apparatus comprises multiple beds containing adsorbent material;

(b) introducing a desorbent stream, which comprises desorbent, into the simulated moving-bed adsorptive apparatus;

(c) withdrawing an extract stream, which comprises desorbent and at least one C8 aromatic, from the simulated moving-bed adsorptive apparatus;

(d) withdrawing at least one raffinate stream, which comprises at least one C8 aromatic, which is different from the C8 aromatic in the extract stream of step (c), from the simulated moving-bed adsorptive apparatus;

(e) maintaining a flow of circulating fluid throughout the simulated moving-bed adsorptive apparatus; and (f) switching the flow of streams into and out of the simulated moving-bed adsorptive apparatus to a bed downstream in terms of the direction of the circulating fluid at set time interval X, wherein the rate flow of at least one of feed introduced in step (a), extract withdrawn in step (C), and raffinate withdrawn in step (d) is varied during time interval X.

22. The process of claim 21, wherein more of the feed stream is introduced into the simulated moving-bed adsorptive apparatus during the latter portion of time interval X than in the earlier portion of time interval X.

23. The process of claim 21, wherein less of the raffinate stream is withdrawn from the simulated moving-bed adsorptive apparatus during the latter portion of time interval X than in the earlier portion of time interval X.

24. The process of claim 21, wherein more of the extract stream is withdrawn from the simulated moving-bed adsorptive apparatus during the latter portion of time interval X than in the earlier portion of time interval X.

* * * * *